(12) United States Patent
Nagatomi

(10) Patent No.: US 9,500,587 B2
(45) Date of Patent: Nov. 22, 2016

(54) SPECIMEN HOLDING CARRIER AND FLUORESCENCE DETECTOR USING SAME

(71) Applicant: Panasonic Intellectual Property Management Co., Ltd., Osaka (JP)

(72) Inventor: Kenji Nagatomi, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 14/439,615

(22) PCT Filed: Oct. 29, 2013

(86) PCT No.: PCT/JP2013/006381
§ 371 (c)(1),
(2) Date: Apr. 29, 2015

(87) PCT Pub. No.: WO2014/068951
PCT Pub. Date: May 8, 2014

(65) Prior Publication Data
US 2015/0276598 A1 Oct. 1, 2015

(30) Foreign Application Priority Data

Oct. 30, 2012 (JP) .................................. 2012-239619
Oct. 30, 2012 (JP) .................................. 2012-239621

(51) Int. Cl.
*G01N 1/28* (2006.01)
*G01N 21/64* (2006.01)
(Continued)

(52) U.S. Cl.
CPC .............. *G01N 21/64* (2013.01); *B01L 3/5085* (2013.01); *B01L 3/545* (2013.01); *B01L 99/00* (2013.01);
(Continued)

(58) Field of Classification Search
CPC .... G01N 1/28; G01N 21/64; G01N 35/0069; G01N 2021/6482; B01L 3/545; B01L 99/00
See application file for complete search history.

(56) References Cited

U.S. PATENT DOCUMENTS

| 4,279,862 A | 7/1981 | Bretaudiere et al. |
| 5,867,474 A | 2/1999 | Nagasawa et al. |

(Continued)

FOREIGN PATENT DOCUMENTS

| EP | 1637872 A1 | 3/2006 |
| EP | 2821779 A1 | 1/2015 |

(Continued)

OTHER PUBLICATIONS

International Search Report PCT/JP2013/006381 dated Feb. 4, 2014.

(Continued)

*Primary Examiner* — David Porta
*Assistant Examiner* — Faye Boosalis
(74) *Attorney, Agent, or Firm* — McDermott Will & Emery LLP

(57) ABSTRACT

A biosensor substrate includes a base substrate to which an excitation light beam is entered, a track formed on the base substrate, and a plurality of wells disposed on the base substrate and accommodating a specimen. A region on which the wells are disposed is sectioned into a plurality of zones in a radial direction, and the wells are arranged on the zones in a circumferential direction. The biosensor substrate is driven at a constant angular velocity while a zone is scanned with the excitation light beam. Velocities set to the zones are varied between the zones, and a zone on the outer radial side has a smaller angular velocity.

10 Claims, 28 Drawing Sheets

(51) Int. Cl.
  *B01L 3/00* (2006.01)
  *G01N 35/00* (2006.01)
  *B01L 99/00* (2010.01)

(52) U.S. Cl.
  CPC ............ *G01N 1/28* (2013.01); *G01N 21/6452* (2013.01); *G01N 35/00069* (2013.01); *B01L 2300/0803* (2013.01); *G01N 2021/6482* (2013.01)

(56) References Cited

U.S. PATENT DOCUMENTS

| | | |
|---|---|---|
| 2004/0264323 A1 | 12/2004 | Worthington et al. |
| 2006/0275181 A1 | 12/2006 | Takeda et al. |
| 2007/0003979 A1 | 1/2007 | Worthington |
| 2011/0189723 A1 | 8/2011 | Yamamura et al. |

FOREIGN PATENT DOCUMENTS

| | | |
|---|---|---|
| JP | 09-282777 A | 10/1997 |
| JP | 2001-238674 A | 9/2001 |
| JP | 2001-243631 A | 9/2001 |
| JP | 2006-153639 A | 6/2006 |
| JP | 2006-322819 A | 11/2006 |
| WO | 2010/027003 A1 | 3/2010 |
| WO | 2013/146364 A1 | 10/2013 |

OTHER PUBLICATIONS

Extended European Search Report that issued in corresponding EP Application No. 13850161.4, dated Jan. 20, 2016.

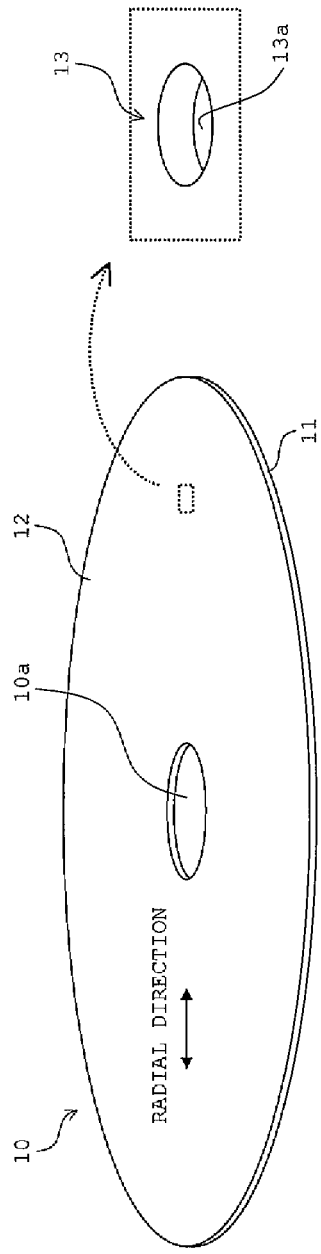
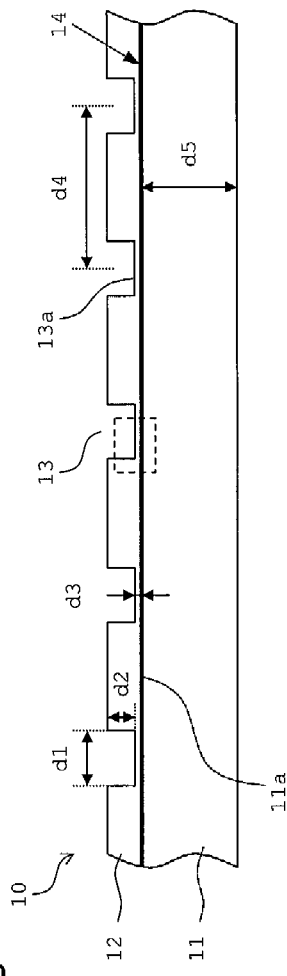
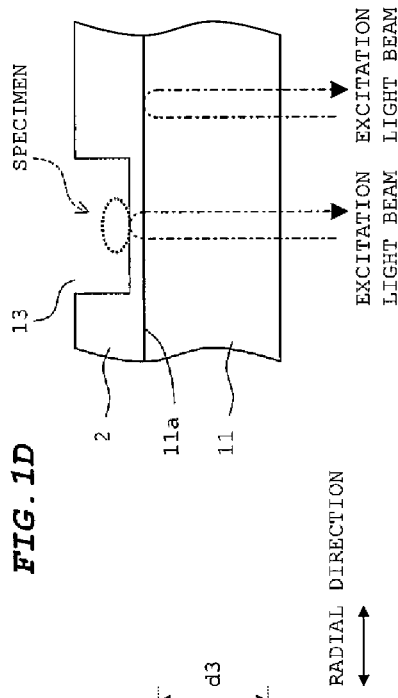
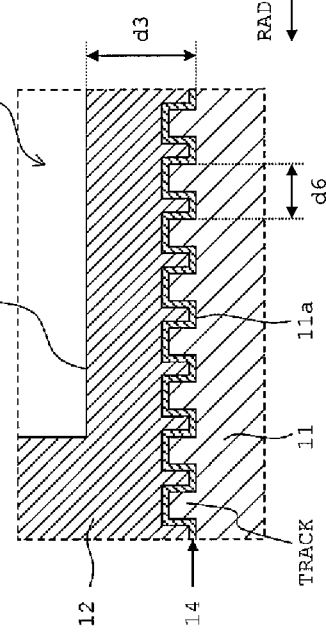
FIG. 1A
FIG. 1B
FIG. 1C
FIG. 1D

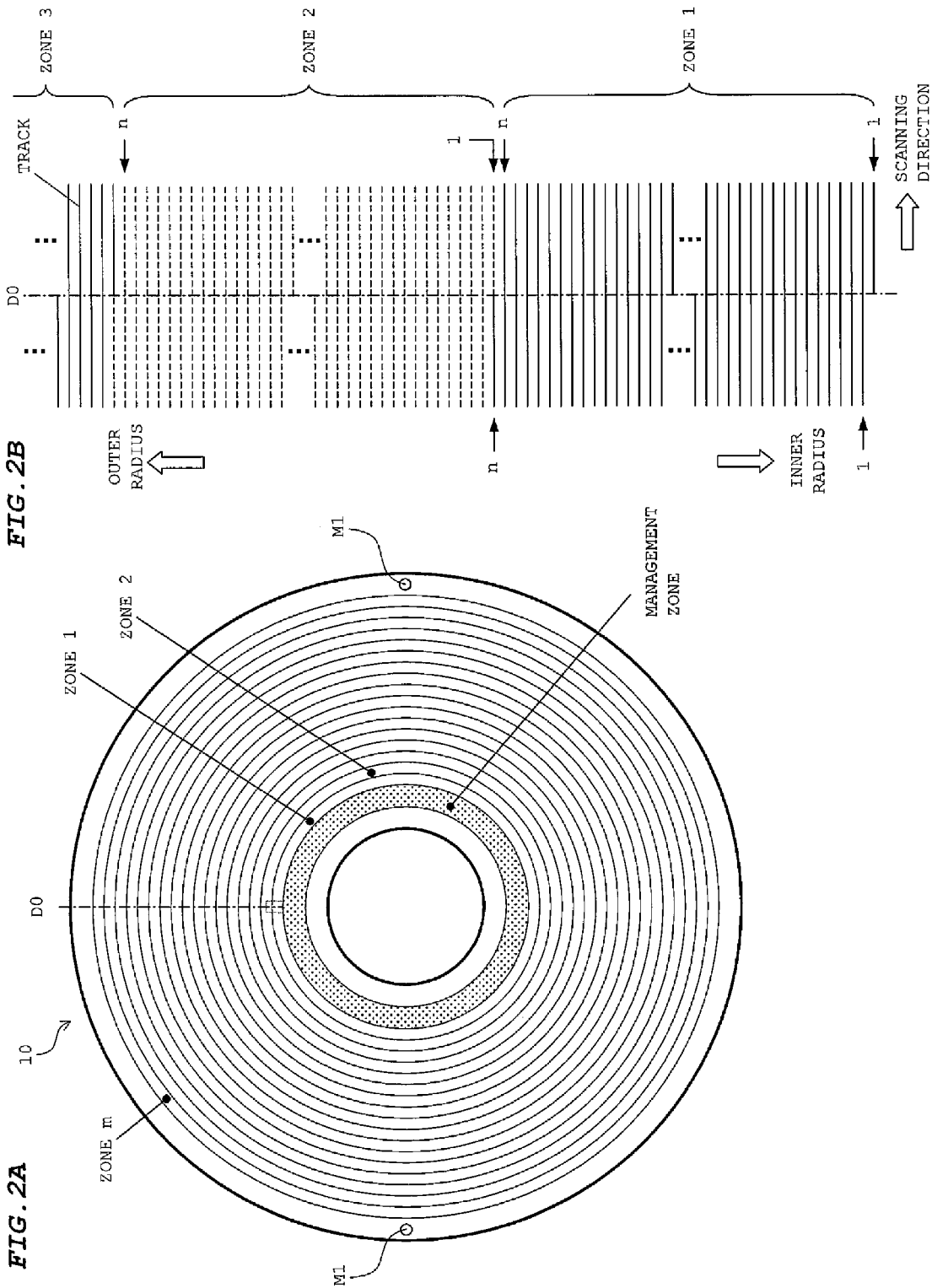

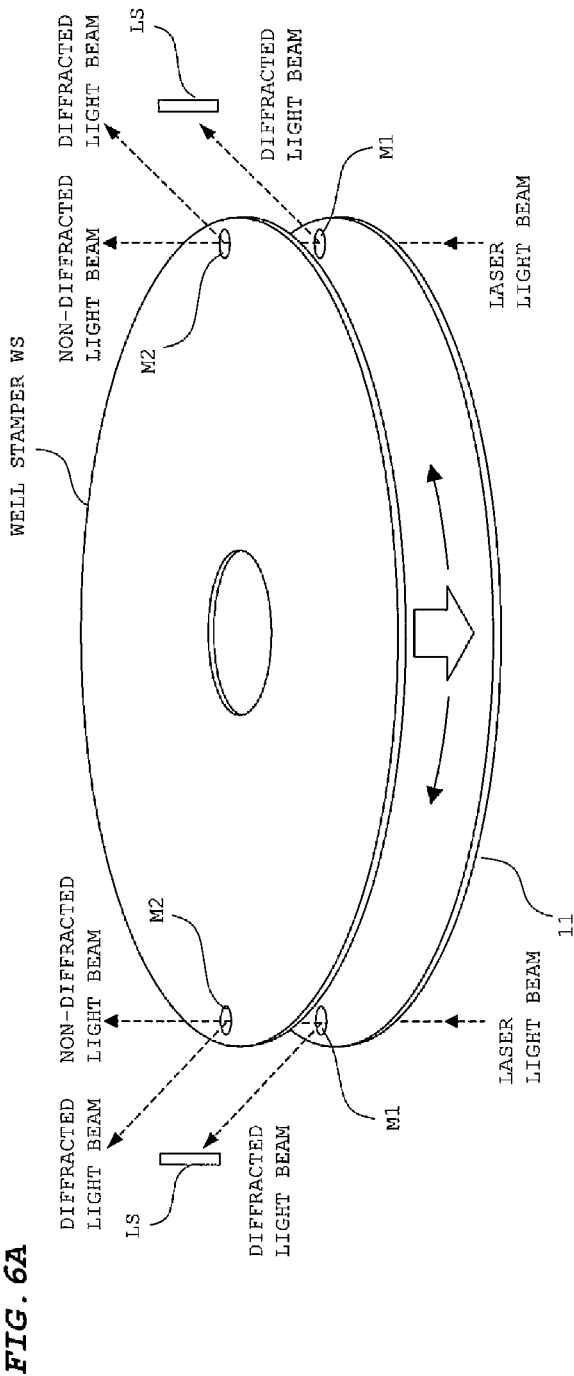
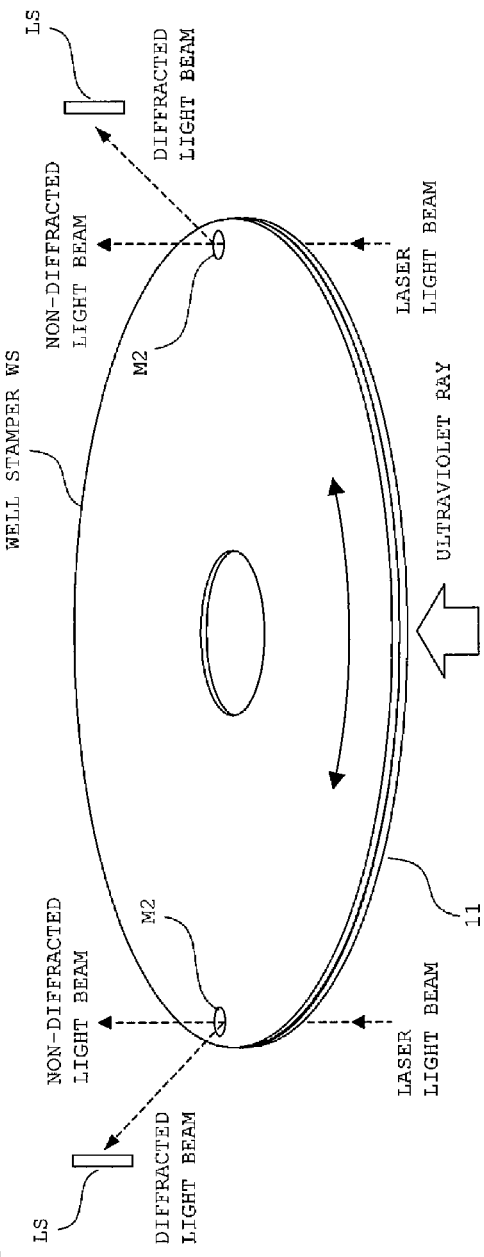
FIG. 6A
FIG. 6B

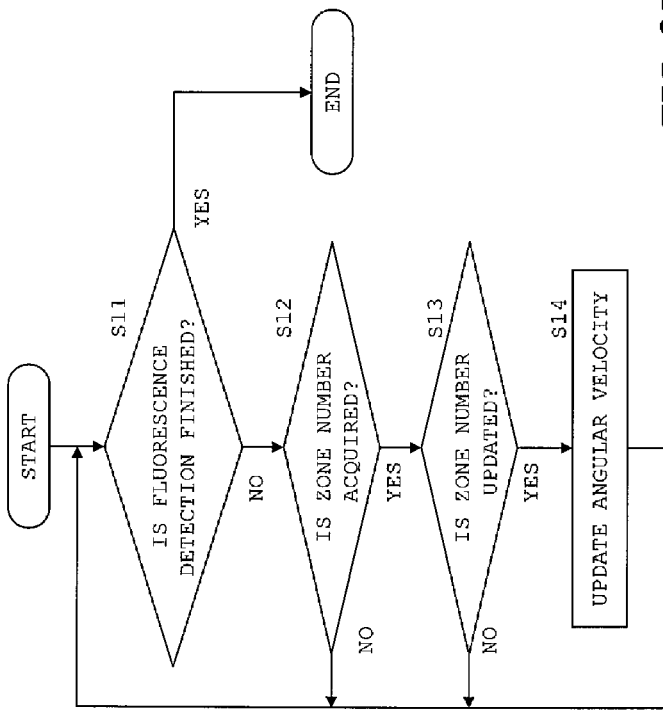
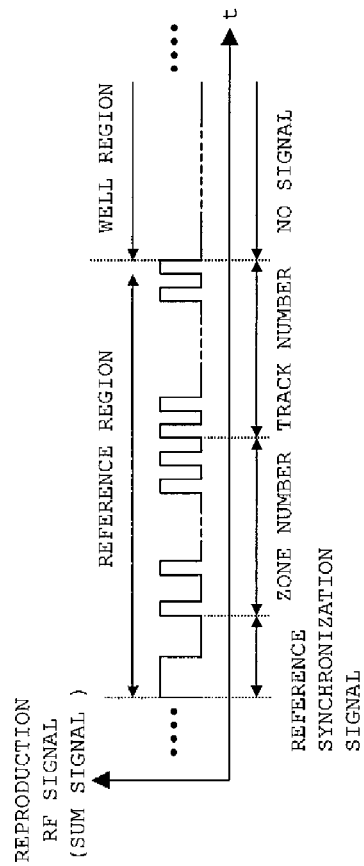
FIG. 8A
FIG. 8B
FIG. 8C

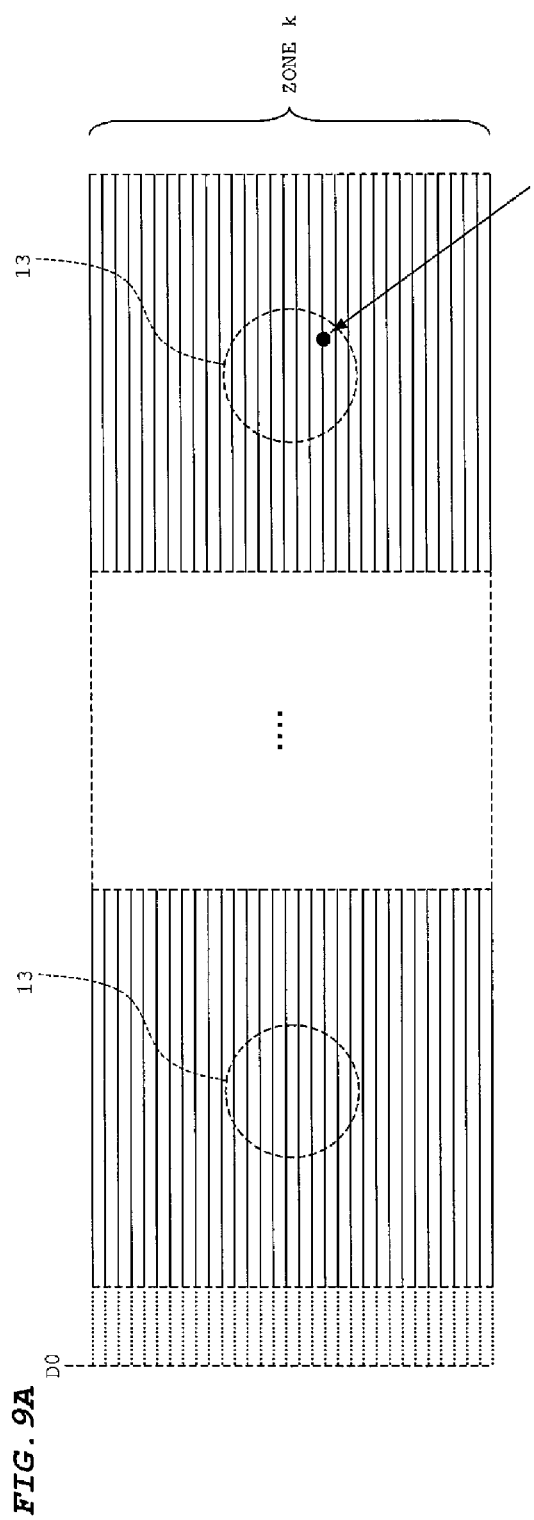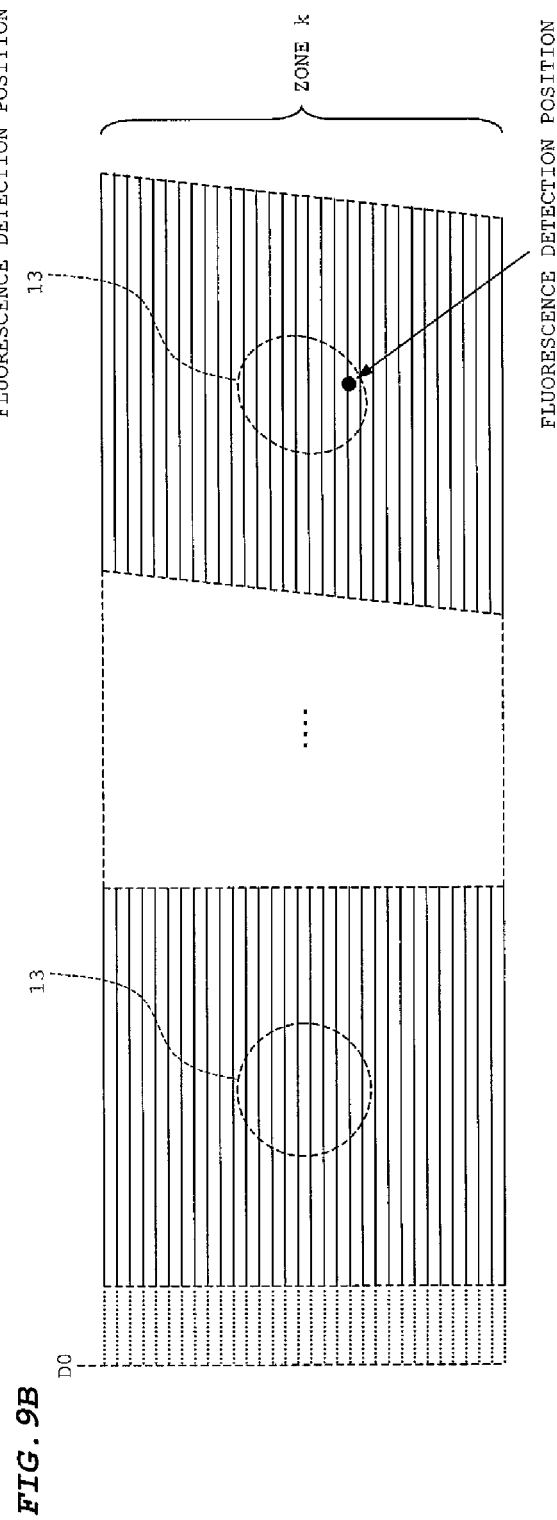

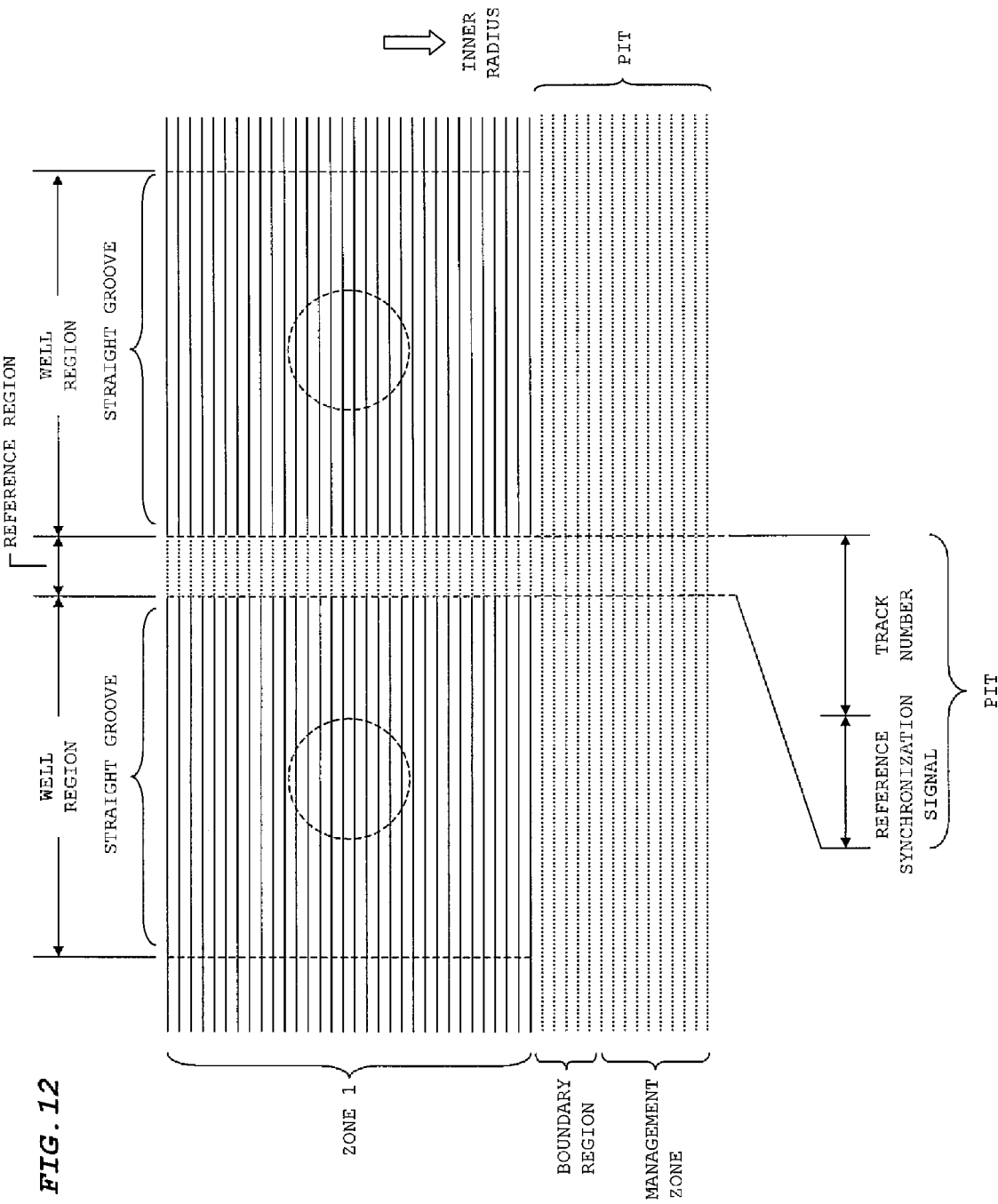

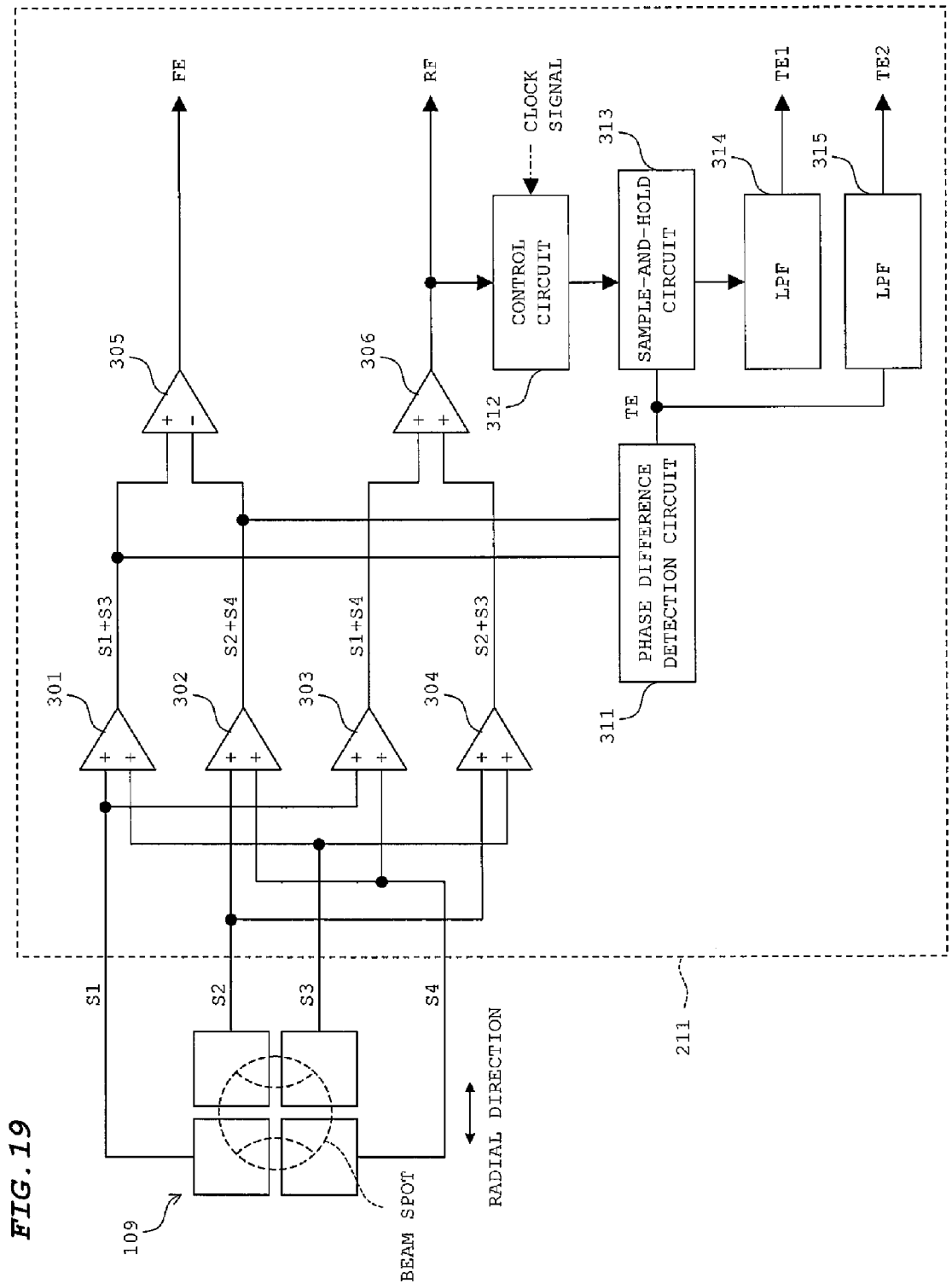

SPECIMEN HOLDING CARRIER AND FLUORESCENCE DETECTOR USING SAME

CROSS-REFERENCE TO RELATED APPLICATIONS

This application is the U.S. National Phase of PCT/JP2013/006381 filed Oct. 29, 2013, which claims priority from Japanese Patent Application No. 2012-239619 filed Oct. 30, 2012, and Japanese Patent Application No. 2012-239621 filed Oct. 30, 2012. The subject matter of each is incorporated herein by reference in entirety.

TECHNICAL FIELD

The present invention relates to a specimen holding carrier that holds a specimen prepared by applying fluorescence labeling to a test specimen such as a cell and a fluorescence detector using the same.

BACKGROUND ART

It is important specifically in the medical field such as a clinical site to detect a cell infected with pathogenic bacteria and a cell in a predetermined form from a large number of cells. As a method for quickly, easily, and highly accurately detecting such a cell, a method below is introduced, for example. In this method, a plurality of micro chambers (wells) is formed on a microarray chip, and fluorescently-labeled cells are filled in the wells. The wells are then observed through a fluorescence microscope while applying a laser light beam, and a certain cell emitting fluorescence is detected.

Moreover, such a configuration is known in which a series of wells filled with cells is scanned with a laser light beam to detect fluorescence emitted from the cells. In this configuration, wells are concentrically formed as the wells are arranged in the radial direction of a disk, and a series of information pits is formed in a track shape on a layer isolated on the light beam incident side from a layer on which the wells are formed as the information pits are arranged along the arrangement of the well. The information pits are formed according to the formats of CDs and DVDs, and the information pits hold information such as address information.

In this configuration, in an optical system that detects fluorescence, a light source that applies a laser light beam to the wells and a light source that applies a laser light beam to the information pits are separately prepared, and the laser light beams emitted from the light sources are converged through a shared objective lens. The objective lens is controlled in such a manner that the laser light beam for information pits is focused on the information pits and caused to follow a series of information pit strings (a track). Thus, a series of the wells is in turn scanned with the laser light beam for wells, and the laser light beam for wells is focused on the cells filled in the wells. When fluorescence is emitted from the cells by applying the laser light beam, this fluorescence is detected by a fluorescence detection photodetector. The presence or absence of a detection target cell is automatically detected out of a large number of cells accommodated in a series of the wells arranged on the disk based on the output from the photodetector, without observation using a fluorescence microscope.

SUMMARY OF INVENTION

A first aspect according to the present invention relates to a specimen holding carrier. The specimen holding carrier according to the aspect includes: a substrate; a track formed to turn around a center of the substrate; and a plurality of specimen accommodating portions disposed on atop face side of the substrate and accommodating a specimen. A region on which the specimen accommodating portions are disposed is sectioned into a plurality of zones in a radial direction; and the specimen accommodating portions are arranged in a circumferential direction of the substrate in the zones.

A second aspect according to the present invention relates to a fluorescence detector that applies a light beam to a specimen holding carrier holding a fluorescently-labeled specimen and detects fluorescence emitted from the specimen by applying the light beam. Here, similarly to the first aspect, the specimen holding carrier includes: a substrate; a track formed to turn around a center of the substrate; and a plurality of specimen accommodating portions disposed on a top face side of the substrate and accommodating a specimen. A region on which the specimen accommodating portions are disposed is sectioned into a plurality of zones in a radial direction; and the specimen accommodating portions are arranged in a circumferential direction of the substrate in the zones. The fluorescence detector according to the second aspect includes: a rotation drive unit configured to rotate the specimen holding carrier; a projection unit configured to cause the light beam to follow the track; a detection unit configured to detect fluorescence emitted from the specimen; and a rotation control unit configured to control the rotation drive unit. The rotation control unit rotates the specimen holding carrier at a same angular velocity in a period in which the light beam is applied to one zone, and changes the angular velocity to the zone so that the angular velocity to the zone becomes smaller as the position at which the zone is disposed goes toward an outer radial side of the substrate.

In the fluorescence detector according to the aspect, the projection unit can be configured to include: a light source configured to emit the light beam; an objective lens configured to converge the light beam on the specimen holding carrier; a lens drive unit configured to drive the objective lens at least in a direction crossing the track; a photodetector configured to receive the light beam reflected on the specimen holding carrier; a signal operating unit configured to generate a tracking error signal expressing positional displacement of a scan position of the light beam to the track in the direction crossing the track based on an output signal of the photodetector; a tracking control unit configured to control the lens drive unit based on the tracking error signal generated at the signal operating unit; and a control switching unit configured to stop control of the lens drive unit based on the tracking error signal and keep a control state of the lens drive unit to a control state before stopped in a period in which the light beam is scanned over a region corresponding to the specimen accommodating portion.

BRIEF DESCRIPTION OF DRAWINGS

FIGS. 1A to 1D are a schematic perspective view of the appearance configuration of a biosensor substrate according to an embodiment, a cross sectional view of the biosensor substrate cut along a plane perpendicular to the surface of the biosensor substrate, a partially enlarged diagram of the cross section of the biosensor substrate, and a schematic diagram of the application state of a laser light beam to a well, respectively.

FIGS. 2A and 2B are a diagram of the area allocation of the biosensor substrate according to the embodiment and a diagram of the relationship between zones and tracks according to the embodiment, respectively.

FIGS. 6A and 6B are diagrams of a fabrication method for the biosensor substrate according to the embodiment.

FIGS. 8A to 8C are a flowchart of the rotation control of the biosensor substrate according to the embodiment and a diagram of the configuration of an angular velocity control table held on a controller.

FIGS. 9A and 9B are diagrams of the effect of the biosensor substrate and the fluorescence detector according to the embodiment.

FIG. 12 is a diagram of the area allocation of the biosensor substrate according to modification 2 and a data format set on a reference region.

FIG. 19 is a diagram of the circuit configuration of a signal operating circuit according to modification 5.

Figure 3:
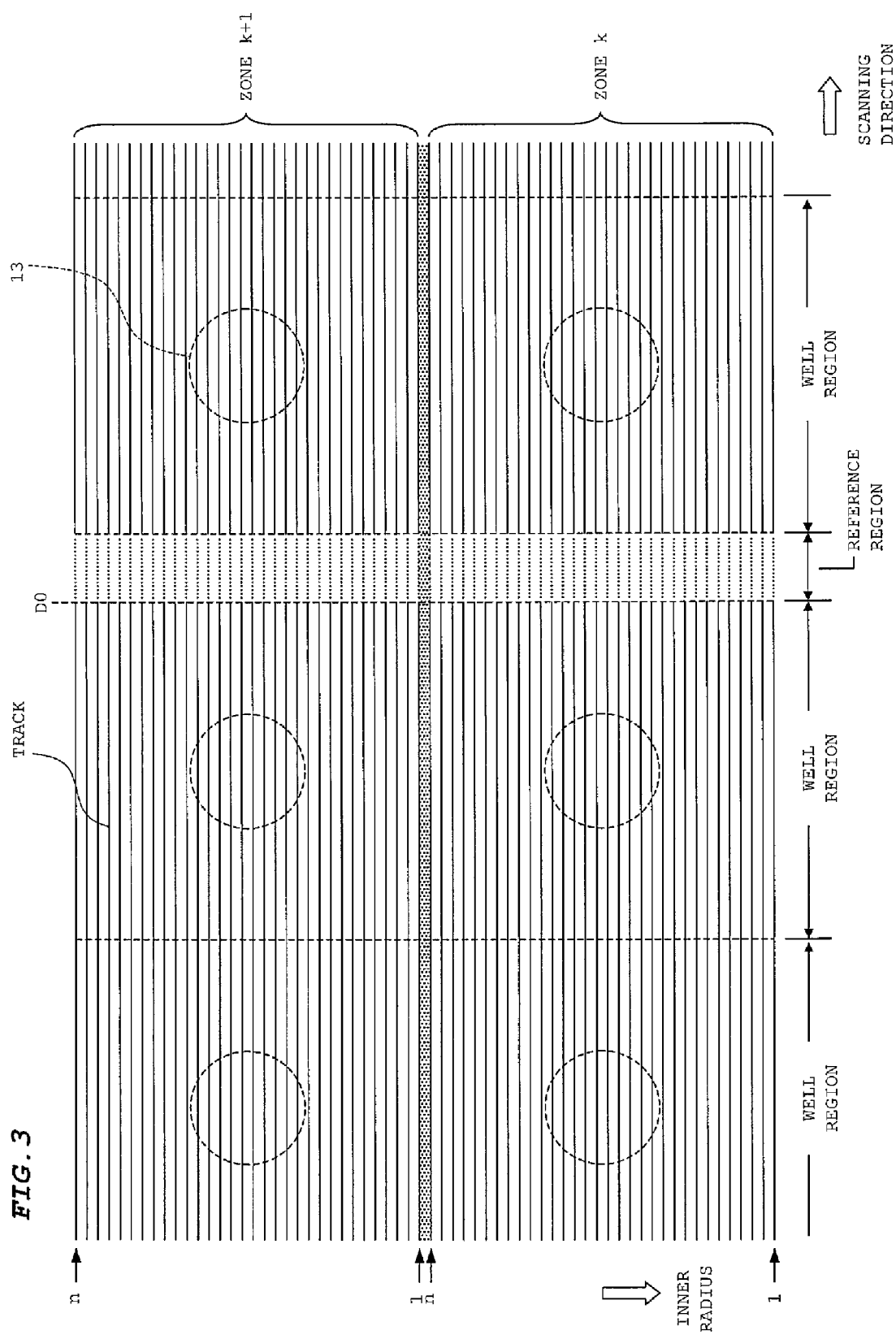
FIG. 3 is a diagram illustrative of the relationship among zones, tracks, well regions, and a reference region according to the embodiment.

However, the drawings are referenced only for explanation, and will not limit the scope of the present invention.

DESCRIPTION OF EMBODIMENTS

In the following, an embodiment of the present invention will be described with reference to the drawings.

In the embodiment shown below, a biosensor substrate 10 corresponds to "a specimen holding carrier" according to the present invention. A base substrate 11 corresponds to "a substrate" according to the present invention. A well 13 corresponds to "a specimen accommodating portion" according to the present invention. A zone number corresponds to "zone identification information" according to the present invention. A semiconductor laser 101 to a photodetector 109 correspond to "a projection unit" according to the present invention. A dichroic prism 106, an objective lens 107, a condenser lens 110, and a fluorescence device 111 correspond to "a detection unit" according to the present invention. A rotating device 123 corresponds to "a rotation drive unit" according to the present invention. A servo circuit 202 and a controller 205 correspond to "a rotation control unit" according to the present invention. The semiconductor laser 101 corresponds to "a light source" according to the present invention. An objective lens actuator 122 corresponds to "a lens drive unit" according to the present invention. A signal operating circuit 211, adders 301 to 304, a phase difference detection circuit 311, and a subtractor 321 correspond to "a signal operating unit" according to the present invention. A servo circuit 212 corresponds to "a tracking control unit" according to the present invention. A controller 215 corresponds to "a tracking control unit" and "a track deviation detection unit" according to the present invention. A control circuit 312 and a sample-and-hold circuit 313 correspond to "a switch control unit" and "a signal holding unit" according to the present invention. A control circuit 331 and a sample-and-hold circuit 332 correspond to "a switch control unit" and "a signal holding unit" according to the present invention. The correspondences between the present invention and the embodiment are only examples, and will not limit the present invention to the embodiment.

<Biosensor Substrate>

FIG. 1A is a schematic perspective view of the appearance configuration of the biosensor substrate 10 according to the embodiment. The biosensor substrate 10 is used to detect red blood cells infected with malaria parasites, for example.

The biosensor substrate 10 has a disk shape similarly to an optical disk (a CD, a DVD, and the like), and a hole 10a in a circular shape is formed in the center. Moreover, the biosensor substrate 10 has a structure in which a well layer 12 is stacked on the top face of the base substrate 11. As illustrated in an enlarged diagram at the right end in FIG. 1A, a plurality of micro wells 13 in a cylindrical hollow is formed on the well layer 12. The wells 13 are arranged nearly concentrically from the inner radius to the outer radius of the biosensor substrate 10. Furthermore, the wells 13 are linearly disposed in the radial direction of the biosensor substrate 10. The well 13 has a bottom portion 13a one step lower than the top face of the well layer 12, and the diameter and the height are set in such a manner that when a specimen is dropped, the specimen can be accommodated.

FIG. 1B is a cross sectional view of the biosensor substrate 10 cut along a plane perpendicular to the surface, and FIG. 1C is an enlarged diagram of a portion shown by a broken line in FIG. 1B.

On the upper side of the base substrate 11 (the well layer 12 side), a spiral track T is formed as similar to an optical disk. A reflective film 14 is disposed between the base substrate 11 and the well layer 12. The reflective film 14 is stacked on the top face of the base substrate 11, and thus a reflection plane 11a that is an interface between the reflective film 14 and the base substrate 11 is formed on the top face of the base substrate 11. The wells 13 are formed on the top face side of the well layer 12 as a predetermined spacing is provided. The bottom portion 13a of the well 13 is positioned slightly on the upper side of the reflective film 14, and the bottom portion 13a of the well 13 is apart from the top face of the reflective film 14.

Here, the diameter and height of the well 13 is defined as d1 and d2, respectively, the spacing between the bottom portion 13a and the reflection plane 11a is defined as d3, the spacing between the wells 13 is defined as d4, the thickness of the base substrate 11 is defined as d5, and the track pitch of the reflection plane 11a is defined as d6. In the embodiment, the diameter d1 and the height d2 are set to 100 μm and 50 μm, respectively, the spacings d3 and d4 are set to 2 μm and 300 μm, respectively, the thickness d5 is set to 0.6 mm, and the track pitch d6 is set to 1 μm. Moreover, the reflectance of the reflective film 14 to an excitation light beam (described later) is set to 3 to 4%.

It is noted that it may be fine that the track pitch d6 is adjusted according to the dimensions of the test specimen that is a target for fluorescence detection. In the embodiment, since the diameter of a red blood cell that is a test specimen is about 10 μm, the track pitch d6 is set to 1 μm in such a manner that the track certainly crosses the test specimen when the specimen is accommodated in the well 13. In other words, it is necessary that the track pitch be set smaller than the width of the test specimen that is a target for fluorescence detection. However, the time necessary to scan the entire region of the biosensor substrate 10 becomes longer as the track pitch becomes smaller. Therefore, in the case where the track pitch d6 is made smaller than the dimensions of the test specimen, it may be fine that the track pitch d6 is set in such a manner that the track crosses test specimens at least one time even though the dimensions of the test specimen are varied.

Moreover, in the embodiment, the base substrate 11 is formed of polycarbonate, the well layer 12 is formed of an ultraviolet curing resin, and the reflective film 14 is formed of a metal such as aluminum and a silver alloy, niobium oxide, a wavelength selection film, and the like. It is noted that the base substrate 11 may be formed of polymethylmethacrylate, amorphous polyolefin, and the like in place of polycarbonate. The well layer 12 may be formed of silicone, polycarbonate, polymethylmethacrylate, amorphous polyolefin, and the like. The film thickness of the reflective film 14 is set to 5 nm to 20 nm, for example, to have a desired reflectance.

FIG. 1(d) is a diagram of the application state of an excitation light beam to the well 13. In the embodiment, an excitation light beam is entered from the base substrate 11 side while the biosensor substrate 10 is rotating, and is converged on the reflective film 14. A part of the incident excitation light beam is reflected on the reflective film 14, and the most part is transmitted through the reflective film 14. The excitation light beam reflected on the reflective film 14 is used for control that the focal point of the excitation light beam is caused to follow the track as described later. Moreover, the excitation light beam transmitted through the reflective film 14 reaches the well 13, and is applied to the specimen accommodated in the well 13. Thus, fluorescence is emitted from the specimen. The fluorescence is used to detect red blood cells infected with malaria parasites included in the specimen as described later.

FIG. 2A is a diagram of the area allocation of the biosensor substrate 10 according to the embodiment, and FIG. 2B is a diagram of the relationship between zones and tracks according to the embodiment.

As illustrated in FIG. 2A, the region on the biosensor substrate 10 is sectioned into m zones in the radial direction from the inner radius to the outer radius. The zones are nearly concentrically set. Moreover, the zones have the same width in the radial direction. In other words, the width of the zones in the radial direction corresponds to the width of n track pitches (n×track pitches).

FIG. 2B is an enlarged diagram of the region depicted by a broken line in FIG. 2A. For convenience, the tracks of zones 1 and 3 are depicted by solid lines, and the tracks of a zone 2 are depicted by broken lines.

Here, as illustrated in FIG. 2A, one of diameters of the biosensor substrate 10 is set to a reference diameter D0. In this case, as illustrated in FIG. 2B, when the track segments of the zones are counted as a track going one round from the position of the reference diameter D0 is one track segment, each of the zones includes n track segments. The beginning edge of the track segment (a track 1) on the innermost radius of the zone 2 is connected to the terminal edge of the track segment (a track n) of zone 1 on the next inside at the position of the reference diameter D0. Similarly in the other the zones, the beginning edge of the track segment (a track 1) on the innermost radius is connected to the terminal edge of the track segment (a track n) of zone 4 on the next inside at the position of the reference diameter D0. As described above, the number of track segments included in the individual zones is n. The width of the zones in the radial direction is set to 300 μm, for example.

FIG. 3 is a diagram of the relationship among the zones, the tracks, well regions, and a reference region according to the embodiment. It is noted that in FIG. 3, in order to easily recognize the boundary between the adjacent zones, the boundary portion is hatched. However, the boundary portion does not have a special structure different from the structure in other portions of the biosensor substrate 10, and the boundary portion also has a structure similar to a portion adjacent to the boundary portion in the radial direction.

As illustrated in FIG. 3, on the biosensor substrate 10, a reference region is set on a region in a predetermined angle range from the reference diameter D0. Tracks included in the reference region are formed of pit strings, and information described later is held on the pit strings. Moreover, tracks included on the regions other than the reference region are formed in grooves (in the following, referred to as "straight grooves") monotonously going in the circumferential direction of the biosensor substrate 10. Similarly to CDs and DVDs, information held on the pit strings on the reference region is reproduced by detecting a change in the intensity of reflected light beam when the track is scanned with an excitation light beam (described later).

Furthermore, as described above, the wells 13 are radially disposed as the wells 13 are arranged at regular intervals in the radial direction of the biosensor substrate 10. Therefore, on the zones, the wells 13 are arranged at constant angle spacings in the circumferential direction. In the embodiment, a region in which the zones are divided at constant angle spacings in the circumferential direction is referred to as a well region. The well region is set in which a region that the reference region is excluded from the zones is equally divided in the circumferential direction by the number of the wells 13 included in the zones. As illustrated in FIG. 3, one well 13 is disposed nearly in the center of one well region.

It is noted that in FIG. 3, the well region is depicted in a square shape. However, strictly speaking, the shape is a pseudo trapezoidal shape in which the edge on the inner radial side of the disk is shorter than the edge on the outer radial side of the disk. In other words, since the well region is formed by dividing ring-shaped zones at constant angle spacings in the circumferential direction, the well has a shape in which the ring is cut at predetermined angles. Therefore, n track portions included in one well region become longer toward the outer radius of the disk.

Moreover, since the well region is set by equally dividing the zone in the circumferential direction as described above, the shapes of the well regions included in the same zone are the same. However, in a different zone, the width of the well region in the circumferential direction is different. The width of the track portion on the well region on the outermost side in the circumferential direction is a quotient of L/j (j is the number of the wells 13 included in the zones) where L is the length obtained by subtracting the width of the reference region from one round of the track on the outermost side of the zone, for example. As described above, since the width of the well region in the circumferential direction is determined by dividing the zone into J portions, in a different zone, the width of the well region in the circumferential direction is different as well. In the embodiment, since the split number j of the zone is the same in all the zones, a zone on the outer radial side has a greater width of the zone in the circumferential direction. In the embodiment, the width of the well region in the circumferential direction is 300 μm or greater.

The width of the well region in the radial direction, that is, the width of the zone in the radial direction is determined by the number n of the track segments included in the zone as described above. In the embodiment, since the track pitch is 1 μm, in the case where the width of the well region in the radial direction is 300 μm, the number of the track portions included in one well region is 300 track portions.

Figure 4:
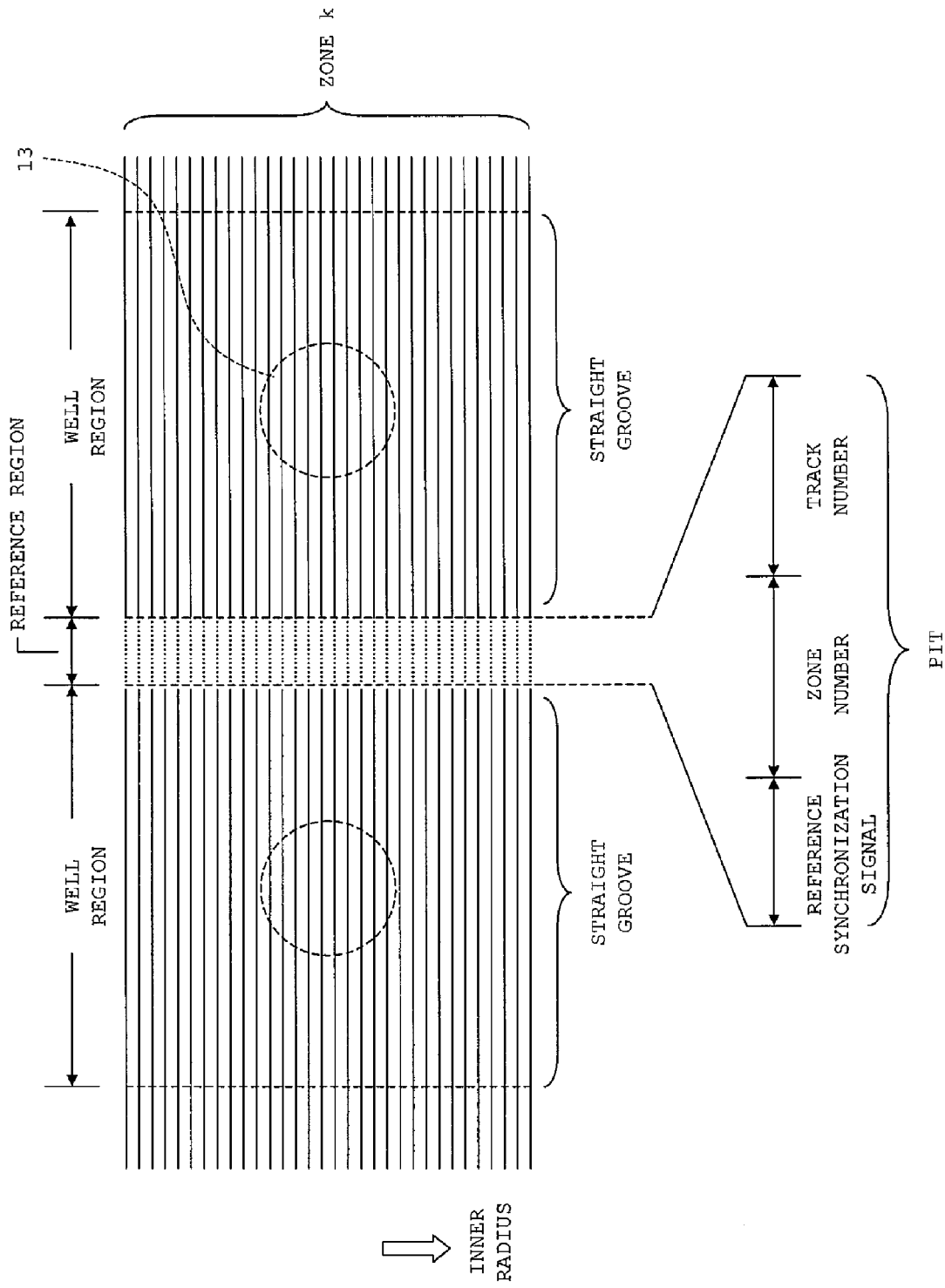
FIG. 4 is a diagram of a data format set on tracks on the reference region according to the embodiment.

FIG. 4 is a diagram of a data format set on the tracks on the reference region according to the embodiment.

As illustrated in FIG. 4, a data format of the track portions included in the reference region is configured in which a reference synchronization signal in a unique pattern is disposed on the beginning followed by a zone number and a track number.

The reference synchronization signal is a unique combination of the length of a pit and the length of a space from this pit to the subsequent pit. This combination is detected, and it is detected that an excitation light beam is scanned over the reference synchronization signal. The zone number is the number of the zone including this track. As illustrated in FIG. 2, for the zone number, the zone number of zone 1 at the position on the innermost radius of the biosensor substrate 10 is defined as one, and the zone number is incremented by one every time when one zone is moved to the outer side. The track number expresses the position of a track in the zone. In other words, the track number of a track at the position on the innermost radius of the zone is one, and the track number is incremented by one every time when one track is moved to the outer side.

The data format illustrated in FIG. 4 is set on the reference region included in all the zones. In the embodiment, the region on the biosensor substrate 10 in which the wells 13 are disposed is divided into zones by the zone number held on the tracks on the reference region, which is not divided into zones by a physical structure. In other words, the zones are set on the region on the biosensor substrate 10 on which the wells 13 are disposed by changing the zone number held on the reference region for the individual zones.

As described above, the region on which the wells 13 are disposed is divided into zones according to the zone numbers.

It is noted that as illustrated in FIG. 2A, on the biosensor substrate 10, a management zone is set further on the inner side of zone 1 disposed on the innermost radius, and a track on which pit strings are spirally arranged is formed on the management zone. The terminal edge of the track on the management zone is connected to the beginning edge of the track on zone 1 on the innermost radius. On the track on the management zone, information that manages the biosensor substrate 10 is held on the pit strings, such as the total number of the zones included in the biosensor substrate 10, and the total number of the wells 13, and the number of the wells 13 included in the zones.

Again referring to FIG. 4, in the embodiment, one well 13 is disposed in the center of the well region as described above. In the embodiment, since the diameter of the well 13 is 100 μm, the well region is sufficiently wider than the well 13. Therefore, even though the position at which the well 13 is disposed on the well region is slightly displaced when the well formed, the well 13 is accommodated in the well region.

FIGS. 5A to 5D are diagrams of a fabrication method for the biosensor substrate 10. It is noted that this fabrication method is almost the same as a fabrication method for an optical disk as shown below.

Figure 5A:
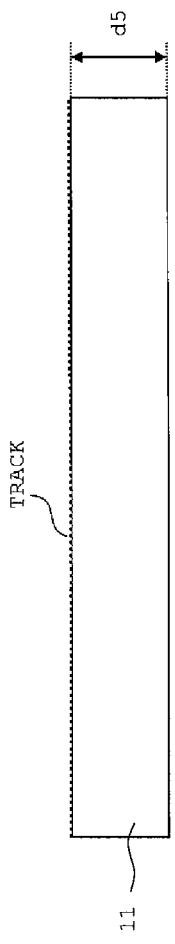
FIGS. 5A to 5D are diagrams of a fabrication method for the biosensor substrate according to the embodiment.
Figure 5B:
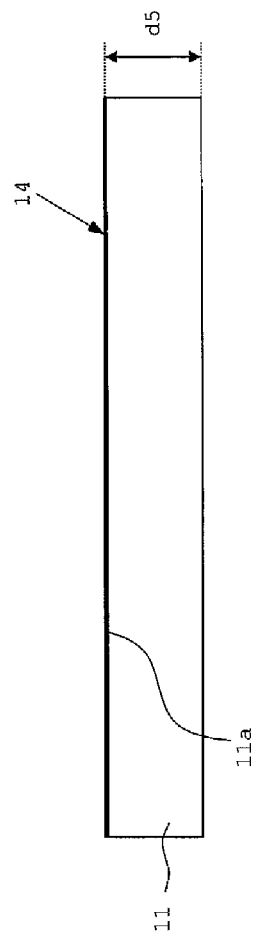
Figure 5C:
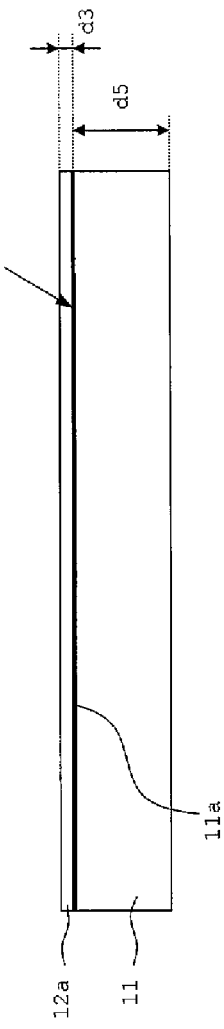
Figure 5D:
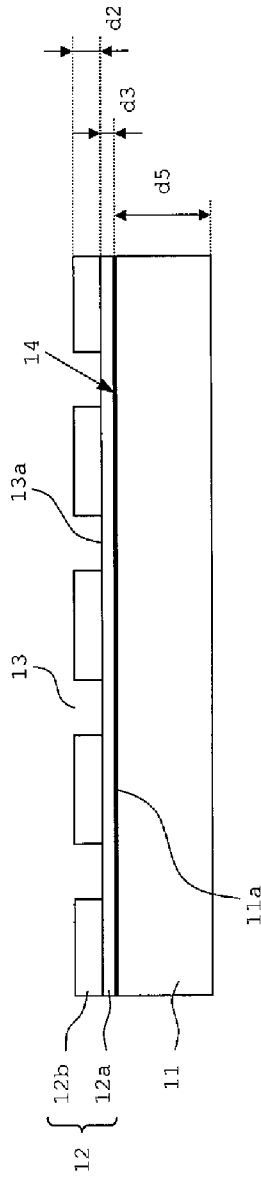

First, as illustrated in FIG. 5A, the base substrate 11 is formed by injection molding. Thus, the thickness of the base substrate 11 is d5, and the track is formed on the top face of the base substrate 11. Subsequently, as illustrated in FIG. 5B, the reflective film 14 is deposited on the top face of the base substrate 11, and thus the reflection plane 11a is formed on the top face of the base substrate 11. Subsequently, as illustrated in FIG. 5c, a bottom layer 12a is stacked on the top face of the reflective film 14 by spin coating. Subsequently, as illustrated in FIG. 5D, a top layer 12b in the thickness d2 is formed on the top face of the bottom layer 12a by photo-polymerization molding. Thus, a plurality of the wells 13 as illustrated in FIG. 1B is formed. The well layer 12 is formed as the bottom layer 12a and the top layer 12b are formed together.

It is noted that in the case where the top layer 12b is formed on the top face of the bottom layer 12a by photo-polymerization molding, it is necessary that a stamper (a well stamper) for photo-polymerization molding be correctly disposed on the base substrate 11 in such a manner that the well 13 is disposed in the center portion of the well region as described above.

FIGS. 6A and 6B are diagrams of an adjustment method for the position of a well stamper WS with respect to the base substrate 11.

In the position adjustment method, on the base substrate 11, two micro diffraction areas M1 to be markers when the position is adjusted are formed at symmetrical positions with respect to the center of the base substrate 11. These diffraction areas M1 are provided by forming diffraction patterns on the outer radius region in which the tracks are not formed on the top face of the base substrate 11 in injection molding. Moreover, the well stamper WS is formed with two micro diffraction areas M2 to be markers at positions corresponding to the diffraction areas M1. Two laser light sources are then disposed at positions at which laser light beams are entered to the two diffraction areas M1 when the base substrate 11 is positioned at a correct position, and the laser light beams are emitted upward from these laser light sources. Furthermore, an optical sensor LS is disposed at positions at which laser light beams diffracted by the diffraction areas M1 and M2 (diffracted light beams) are received.

In photo-polymerization molding, first, as illustrated in FIG. 6A, the position of the base substrate 11 in the circumferential direction is adjusted in order that the diffracted light beams generated through the two diffraction areas M1 are individually received at the optical sensors LS. At this time, apart of the laser light beams (the zeroth order diffracted light beam: a non-diffracted light beam) is not diffracted by the diffraction areas M1, and transmitted through the diffraction areas M1 as it is. Subsequently, the well stamper WS is brought close to the top face of the base substrate 11, and at the same time, the position of the well stamper WS in the circumferential direction is adjusted in order that the non-diffracted light beams transmitted through the diffraction areas M1 are entered to the diffraction areas M2. In other words, the position of the well stamper WS in the circumferential direction is adjusted in such a manner that the non-diffracted light beams are entered, the diffracted light beams are generated through the two diffraction areas M2, and the diffracted light beams are individually received at the optical sensors LS. In this manner, the well stamper WS is pressed against the top face of the base substrate 11 in the state in which the positions of the base substrate 11 and the well stamper WS are adjusted. In this state, ultraviolet rays are applied to cure an ultraviolet curing resin, and then the top layer 12b is formed.

It is noted that the positioning between the base substrate 11 and the well stamper WS may be performed by a method other than the method described above. For example, it may be fine that projections and recesses are provided on the well stamper WS and the base substrate 11, the projections are fit into the recesses, and the positioning between the base substrate 11 and the well stamper WS is performed.

<Fluorescence Detector>

Figure 7:
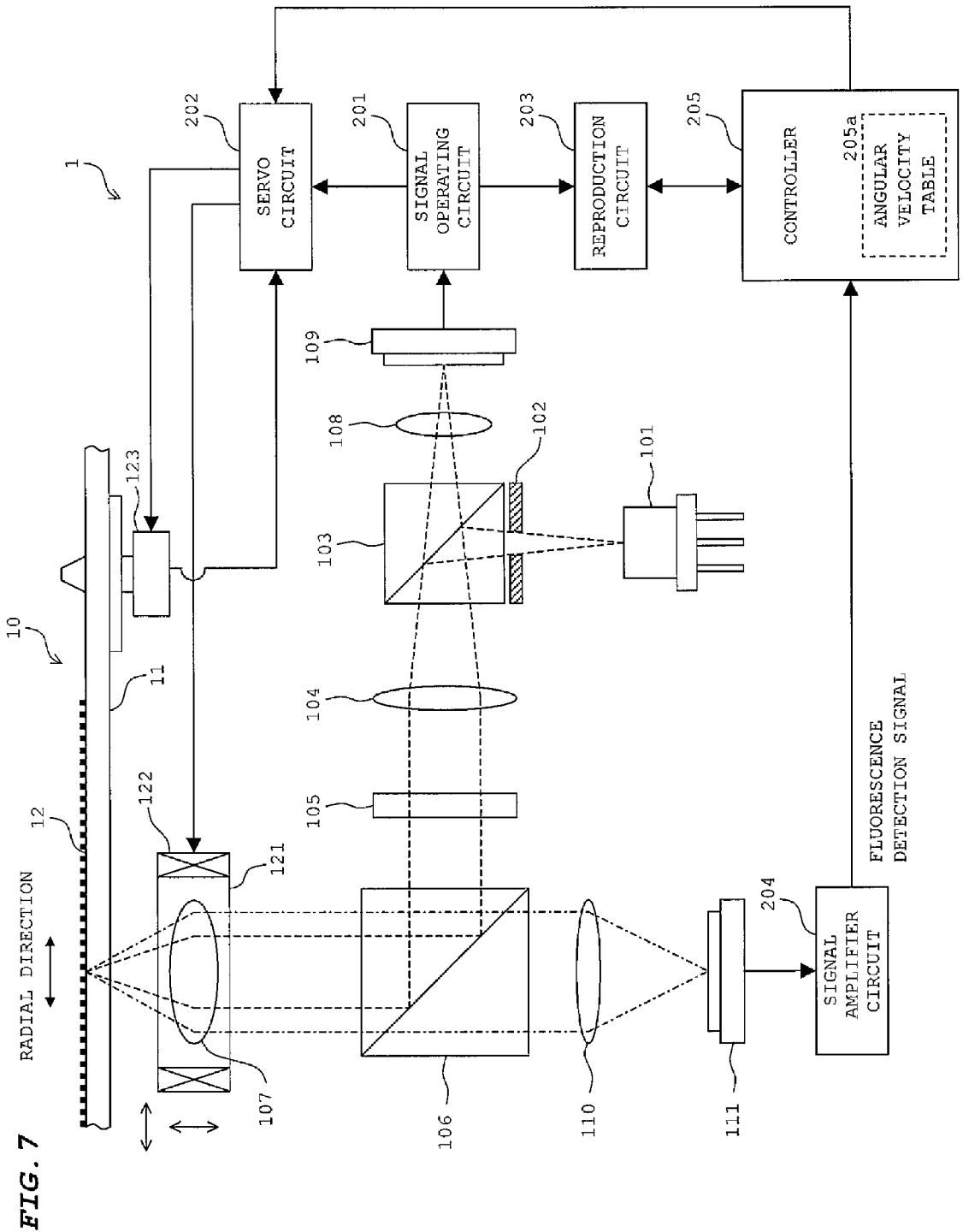
FIG. 7 is a diagram of the configuration of a fluorescence detector according to the embodiment.

FIG. 7 is a diagram of the configuration of a fluorescence detector 1 according to the embodiment. For example, the fluorescence detector 1 is used for determining whether red blood cells accommodated in the wells 13 on the biosensor substrate 10 are infected with malaria parasites.

In the use of the fluorescence detector 1, a specimen prepared by applying fluorescence labeling to a test specimen is accommodated in the wells 13 on the biosensor substrate 10 in advance. In the embodiment, fluorescence labeling is applied to a red blood cell that is a test specimen in a diameter of about 10 µm and a thickness of about 2 µm, and a plurality of these red blood cells is disposed on the bottom portion 13a of the well 13 in a diameter of 100 µm in parallel with one another. A hole 10a of the biosensor substrate 10 on which the specimen is accommodated (see FIG. 1A) is set on a rotating device 123 (a turntable) of the fluorescence detector 1, and measurement is started.

The optical system of the fluorescence detector 1 includes a semiconductor laser 101, an aperture 102, a polarization beam splitter (PBS) 103, a collimator lens 104, a quarter-wave plate 105, a dichroic prism 106, an objective lens 107, an anamorphic lens 108, a photodetector 109, a condenser lens 110, and a fluorescence device 111. Moreover, in addition to the optical system described above, the fluorescence detector 1 includes a holder 121, an objective lens actuator 122, a rotating device 123, a signal operating circuit 201, a servo circuit 202, a reproduction circuit 203, a signal amplifier circuit 204, and a controller 205.

The optical system of the fluorescence detector 1, the holder 121, and the objective lens actuator 122 are disposed in a housing similarly to an existing optical pickup device used for recording/reproduction of CDs and DVDs. Furthermore, this housing is movable in the radial direction of the biosensor substrate 10 by a predetermined guide mechanism.

The semiconductor laser 101 emits a laser light beam at a wavelength of about 405 nm (in the following, referred to as "an excitation light beam"). It is noted that the excitation light beam in the embodiment is an example of a light beam described in claims. In FIG. 7, in the excitation light beam emitted from the semiconductor laser 101, an excitation light beam guided to the biosensor substrate 10, that is, an excitation light beam passed through the aperture 102 is depicted by broken lines. A circular opening having a predetermined diameter is formed on the aperture 102, and the aperture 102 limits the diameter of the excitation light beam. Moreover, the position of the semiconductor laser 101 is adjusted in such a manner that the excitation light beam emitted from the semiconductor laser 101 is an S-polarized light beam with respect to PBS 103. Thus, after the diameter of the excitation light beam emitted from the semiconductor laser 101 is limited by the aperture 102, the excitation light beam is reflected on the PBS 103, and entered to the collimator lens 104.

The collimator lens 104 converts the excitation light beam entered from the PBS 103 side into a collimated light beam. Thus, the excitation light beam passed through the collimator lens 104 is a collimated light beam in a predetermined diameter. The quarter-wave plate 105 converts the excitation light beam entered from the collimator lens 104 side into a circularly polarized light beam, and converts the excitation light beam entered from the dichroic prism 106 side into a linear polarized light beam orthogonal to the polarization direction when entered from the collimator lens 104 side. Thus, the excitation light beam entered from the collimator lens 104 side to the PBS 103 is transmitted through the PBS 103.

The dichroic prism 106 is configured in which a light beam at a wavelength of about 405 nm is reflected and light beams at wavelengths from about 450 to 540 nm are transmitted. Thus, the excitation light beam entered from the quarter-wave plate 105 side is reflected on the dichroic prism 106, and entered to the objective lens 107.

The objective lens 107 is configured to correctly converge the excitation light beam on the biosensor substrate 10. More specifically, the objective lens 107 is configured in which the excitation light beam entered from the dichroic prism 106 side is converged at a predetermined NA (a numerical aperture, it is 0.34, here). The incident diameter of the excitation light beam to the objective lens 107 is determined by the diameter of the aperture 102. The focal depth of the excitation light beam converged through the objective lens 107 is determined by the NA of the excitation light beam.

The objective lens 107 is driven by the objective lens actuator 122 in the focus direction (the direction perpendicular to the biosensor substrate 10) and the tracking direction (the radial direction of the biosensor substrate 10) in the state in which the objective lens 107 is held on the holder 121. In other words, the objective lens 107 is driven in such a manner that the excitation light beam follows the track formed of pit strings in the state in which the excitation light beam is focused on the reflection plane 11a of the biosensor substrate 10. A part of the excitation light beam focused on the reflection plane 11a is reflected on the reflection plane 11a, and the most part is transmitted through the reflection plane 11a.

The excitation light beam reflected on the reflection plane 11a (in the following, referred to as "the reflected excitation light beam") is reflected on the dichroic prism 106, converted into a linear polarized light beam at the quarter-wave plate 105, and formed into a converged light beam by the collimator lens 104. The reflected excitation light beam entered from the collimator lens 104 side to the PBS 103 is then transmitted through the PBS 103 as described above.

The anamorphic lens 108 introduces astigmatism into the reflected excitation light beam entered from the PBS 103 side. The reflected excitation light beam transmitted through the anamorphic lens 108 is entered to the photodetector 109. The photodetector 109 includes a quadrant sensor that receives the reflected excitation light beam on the light receiving surface. The detection signal of the photodetector 109 is inputted to the signal operating circuit 201.

In the excitation light beam applied to the biosensor substrate 10, the excitation light beam transmitted through the reflection plane 11a reaches the bottom portion 13a of the well 13. In the embodiment, the focal depth of the excitation light beam is longer than the spacing d3 in FIG. 1B. Therefore, when the excitation light beam focused on the reflection plane 11a is transmitted through the reflection plane 11a, the excitation light beam reaches the bottom portion 13a of the well 13 as the excitation light beam is not spread from nearly in the focused state, and the excitation light beam is applied to the specimen.

When the excitation light beam is applied to fluorescently-labeled red blood cells disposed on the bottom portion 13a in parallel with one another and infected with malaria parasites, fluorescence is emitted from malaria parasites. This fluorescence has an NA (a numerical aperture) greater than the NA of the excitation light beam as depicted by alternate long and short dash lines in FIG. 7. Therefore, the beam diameter of fluorescence is greater than the beam diameter of the excitation light beam between the objective lens 107 and the dichroic prism 106. The NA of fluorescence is 0.65, for example. Moreover, the wavelength of fluorescence is different from the wavelength of the excitation light beam, and is in a renege of wavelengths from 450 to 540 nm in the embodiment.

Since fluorescence entered from the objective lens 107 side to the dichroic prism 106 has wavelengths from 450 to 540 nm, the fluorescence is transmitted through the dichroic prism 106. The condenser lens 110 condenses fluorescence entered from the dichroic prism 106 side, and guides the condensed fluorescence to the fluorescence device 111. The fluorescence device 111 includes a sensor that receives fluorescence on the light receiving surface. The detection signal of the fluorescence device 111 is inputted to the signal amplifier circuit 204.

The signal operating circuit 201 generates a focus error signal FE and a tracking error signal TE from the detection signal of the photodetector 109, and generates a reproduction RF signal from the detection signal of the photodetector 109. The focus error signal is generated using an existing astigmatism method used in the optical disk techniques. Moreover, the tracking error signal is generated using an existing one-beam push-pull method used in the optical disk techniques.

The servo circuit 202 controls the driving of the objective lens actuator 122 using the focus error signal FE and the tracking error signal TE outputted from the signal operating circuit 201 in such a manner that the focal point of the excitation light beam follows the track of the biosensor substrate 10. Moreover, the servo circuit 202 controls the rotating device 123 in such a manner that the biosensor substrate 10 is rotated at a constant angular velocity in the individual zones. The rotating device 123 outputs a rotation detection signal to the servo circuit 202 every time when the biosensor substrate 10 makes one turn. The servo circuit 202 rotates the biosensor substrate 10 using the rotation detection signal in such a manner that the angular velocity is constant in the individual zones.

As described later, in the embodiment, in the period in which the excitation light beam is included in the same zone, the biosensor substrate 10 is rotated and driven at an angular velocity set to the zone. Angular velocities set to the zones are varied in the individual zones. In other words, the angular velocities set to the zones are lower in the zones on the outer radius side. In the embodiment, the angular velocity is set to the zones in such a manner that the linear velocity when the excitation light beam is scanned over the track on the innermost radius of the individual zones is the same between the zones.

The reproduction circuit 203 demodulates the reproduction RF signal outputted from the signal operating circuit 201, and generates reproduction data. The reproduction data to be demodulated is the zone number and the track number held on the tracks (the pit strings) in the reference region. The reproduction circuit 203 outputs the demodulated zone number and the track number to the controller 205. The signal amplifier circuit 204 amplifies the detection signal of the fluorescence device 111 (a fluorescence detection signal), and outputs the signal to the controller 205. The fluorescence detection signal is used to identify red blood cells infected with malaria parasites included in the specimen.

The controller 205 controls the units of the fluorescence detector 1 in addition to the signal operating circuit 201, the servo circuit 202, and the reproduction circuit 203. The controller 205 includes a CPU and a memory, and controls the units according to programs stored on the memory. Moreover, the controller 205 holds an angular velocity table 205a that regulates the angular velocity in the zones. In the case where the scan position of the excitation light beam is moved from one zone to another zone, the controller 205 updates the angular velocity of the biosensor substrate 10 in reference to the angular velocity tables 205a.

FIG. 8A is a flowchart of the update control of the angular velocity according to the embodiment. FIG. 8B is a diagram of the structure of the angular velocity table 205a held on the controller 205. As illustrated in FIG. 8B, on the angular velocity table 205a, angular velocities are described in association with the zone numbers.

Referring to FIG. 8A, the controller 205 waits for the output of the zone number from the reproduction circuit 203 (S12) until the fluorescence detection operation is finished (S11).

FIG. 8C is a schematic waveform diagram of the transition of the reproduction RF signal outputted from the signal operating circuit 201 to the reproduction circuit 203 (a SUM signal that signals outputted from the sensors of the quadrant sensor disposed on the photodetector 109 are added). When the reproduction circuit 203 detects a reference synchronization signal having a unique pattern on the reproduction RF signal, the reproduction circuit 203 demodulates a zone number from the reproduction RF signal included in a range of a predetermined period from the reference synchronization signal, and then demodulates a track number from the reproduction RF signal included in a range of a predetermined period. It is noted that since the tracks included in the well region are straight grooves with no pits as described above, signals expressing pits do not appear on the reproduction RF signal in the period in which the excitation light beam is scanned over the well region.

When the controller 205 acquires the zone number from the reproduction circuit 203 (S12: YES), the controller 205 determines whether the acquired zone number is changed from the previously acquired zone number (S13). Here, when the zone number is not changed (S13: NO), the controller 205 returns the process to S11, and waits for the arrival of the next zone number. On the other hand, when the zone number is changed, the controller 205 acquires the angular velocity corresponding to the zone number acquired this time from the angular velocity table 205a, and updates the angular velocity of the biosensor substrate 10 to the acquired angular velocity (S14).

After that, the controller 205 again returns the process to S11, and waits for the arrival of a zone number until the fluorescence detection operation is finished (S21). It is noted that in the determination in S11, YES is determined, for example, in the case where the scanning of the track on the outermost radius of the last zone acquired from the management zone with the excitation light beam is finished. When a new zone number is acquired (S12: YES), the controller 205 performs the processes after S13. Meanwhile, when the fluorescence detection operation is finished (S11: YES), the controller 205 ends the update process of the angular velocity.

Effect of the Embodiment

As described above, in the fluorescence detector 1 according to the embodiment, since the angular velocity to the zone is changed in such a manner that the angular velocity is more decreased with respect to the zone as the position at which the zone is disposed goes toward the outer radial side of the biosensor substrate 10, also in the case where a light beam is applied to the outer radial portion of the biosensor substrate 10, the scanning rate of the light beam to the wells 13 is not excessively increased. Therefore, also on the outer radial portion of the biosensor substrate 10, a sufficient quantity of an excitation light beam can be applied to the specimen accommodated in the wells 13. Moreover, in the zone, since the biosensor substrate 10 is rotated at a constant angular velocity, the time necessary to scan one zone is shortened as compared with the case where the zones are scanned at a constant linear velocity set to the track on the innermost radius of the individual zones. Therefore, the time necessary to scan the entire region of the biosensor substrate 10 with a light beam can be shortened, and the detection time to the biosensor substrate 10 can be shortened.

As described above, in the fluorescence detector 1 according to the embodiment, an excitation light beam can be correctly and efficiently applied to the specimen across the entire region from the inner radial portion to the outer radial portion of the biosensor substrate 10.

It is noted that according to the embodiment, since the zones are scanned at a constant angular velocity, the time to scan one round of the track with an excitation light beam is the same in the zone. Therefore, in the case where fluorescence detection signal outputted from the signal amplifier circuit 204 is sampled in a predetermined sampling period and a sample value is acquired, the number of sample values acquired in a time period in which an excitation light beam goes round a track one time from the reference diameter D0 in FIG. 2A is the same in the zones. Moreover, since the angular velocity set to the zones is adjusted in such a manner that the same linear velocity is set to the track on the innermost radius of the individual zones, the number of sample values acquired in a time period in which the excitation light beam makes one round from the reference diameter D0 is also the same among the zones. Therefore, in the embodiment, the number of sample values acquired in a time period in which the excitation light beam makes one round from the reference diameter D0 is the same at given positions of in the radial direction.

Therefore, when sample values acquired in a period in which the excitation light beam makes one round from the reference diameter D0 are mapped on the memory every other lines as described above, the period from the beginning edge of the line to the edge of the well 13 on the innermost radial side (the number of samples) is the same as the period from the beginning edge of the line to the edge of the well 13 on the outermost radial side (the number of samples). Therefore, on the sample values mapped on the memory, the region corresponding to the well 13 can be defined as a circular shape similarly to the wells 13 on the biosensor substrate 10. Therefore, when the sample values mapped on the memory are reproduced as an image, as schematically illustrated in FIG. 9A, the regions of the wells 13 can be expressed as a circular region on the zones.

On the other hand, in the case where the zones are scanned at a constant linear velocity, the time to scan one round of the track with an excitation light beam becomes longer, as the scan position goes toward the outer radius. Therefore, in the case where the fluorescence detection signal outputted from the signal amplifier circuit 204 is sampled in a predetermined sampling period and a sample value is acquired, the number of sample values acquired in a time period in which the excitation light beam makes one round from the reference diameter D0 is greater on the outer radial side in the zone.

Thus, when sample values acquired in a period in which the excitation light beam makes one round from the reference diameter D0 are mapped on the memory every other lines, the period from the beginning edge of the line to the edge of the well 13 on the innermost radial side (the number of samples) is different from the period from the beginning edge of the line to the edge of the well 13 on the outermost radial side (the number of samples). Therefore, on the sample values mapped on the memory, the region corresponding to the well 13 is an elliptic region in a distorted circular shape, different from the wells 13 on the biosensor substrate 10. Thus, when the sample values mapped on the memory are reproduced as an image, as schematically illustrated in FIG. 9B, the region of the well 13 is displayed as a region distorted in an elliptic shape on the zones.

As described above, when the region of the well 13 is displayed in a shape distorted in an elliptic shape, since the well 13 displayed on the image is different from the shape of the well 13 visually recognized through an electron microscope in the confirmation that red blood cells infected with malaria parasites are actually visually recognized through the electron microscope after the test using the fluorescence detector 1, it is difficult to make identification between the position in the well 13 at which an abnormality is detected in the test using the fluorescence detector 1 and the position in the well 13 in observation through the electron microscope.

On the other hand, according to the embodiment, since the region of the well 13 can be displayed in a circular shape as described above, it is easy to make identification between the position in the well 13 at which an abnormality is detected in the test using the fluorescence detector 1 and the position in the well 13 in observation through the electron microscope. As described above, according to the embodiment, such an effect can be further exerted that operations to confirm the test result using the fluorescence detector 1 in the actual observation are facilitated.

<Modification 1>

Figure 10:
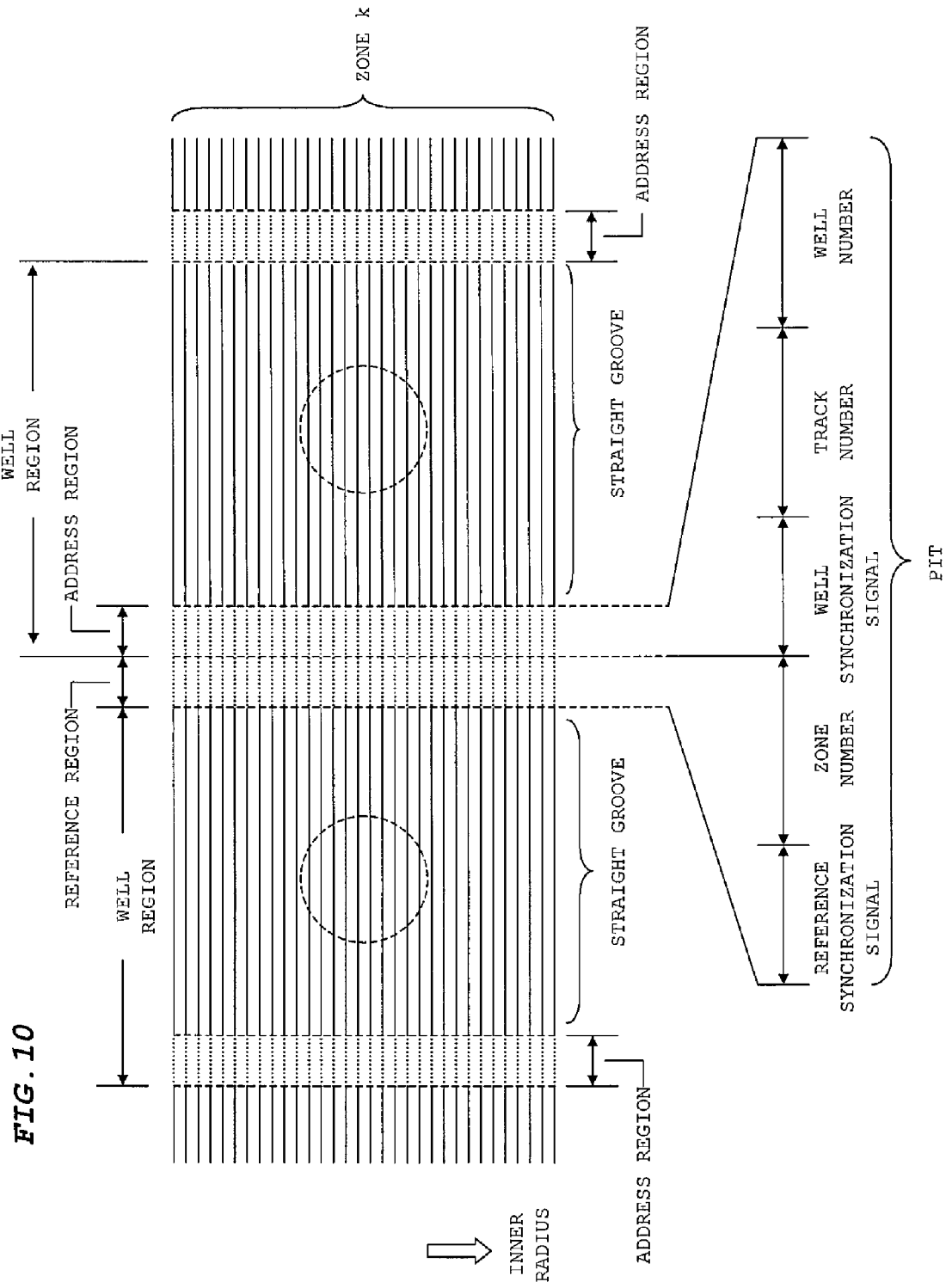
FIG. 10 is a diagram of the configuration of a biosensor substrate according to modification 1 and data formats set on a reference region and an address region.

FIG. 10 is a diagram of the configuration of a biosensor substrate 10 according to modification 1 and data formats set on the reference region and the address region.

In the modification, an address region is provided at the beginnings of the well regions separately from the reference region. The address region is disposed to extend in the radial direction of the biosensor substrate 10 at a predetermined angle width. Moreover, similarly to the reference region, pit strings are formed along tracks also on the address region, and a predetermined item of information is held on the pit strings.

In the modification, track numbers held on the tracks on the reference region are held on the tracks on the address region. Furthermore, the number of the well 13 included in the well region (a well number) is held on the tracks on the address region. In the modification, the well number is set on the individual zones. In other words, the well number of a well 13 that appears first in the scanning direction from the start position of the zones is set to one, and the well number is incremented by one every time when a well 13 appears in the scanning direction.

In the modification, the update process of the angular velocity is similar to the embodiment described above. According to the modification, since the track number and the well number are allocated to the individual wells 13, the well 13 is easily identified, and the track crossing the well 13 is easily identified. Therefore, in the case where red blood cells infected with malaria parasites are detected in the well 13, the position of the red blood cells is easily and correctly identified.

<Modification 2>

Figure 11:
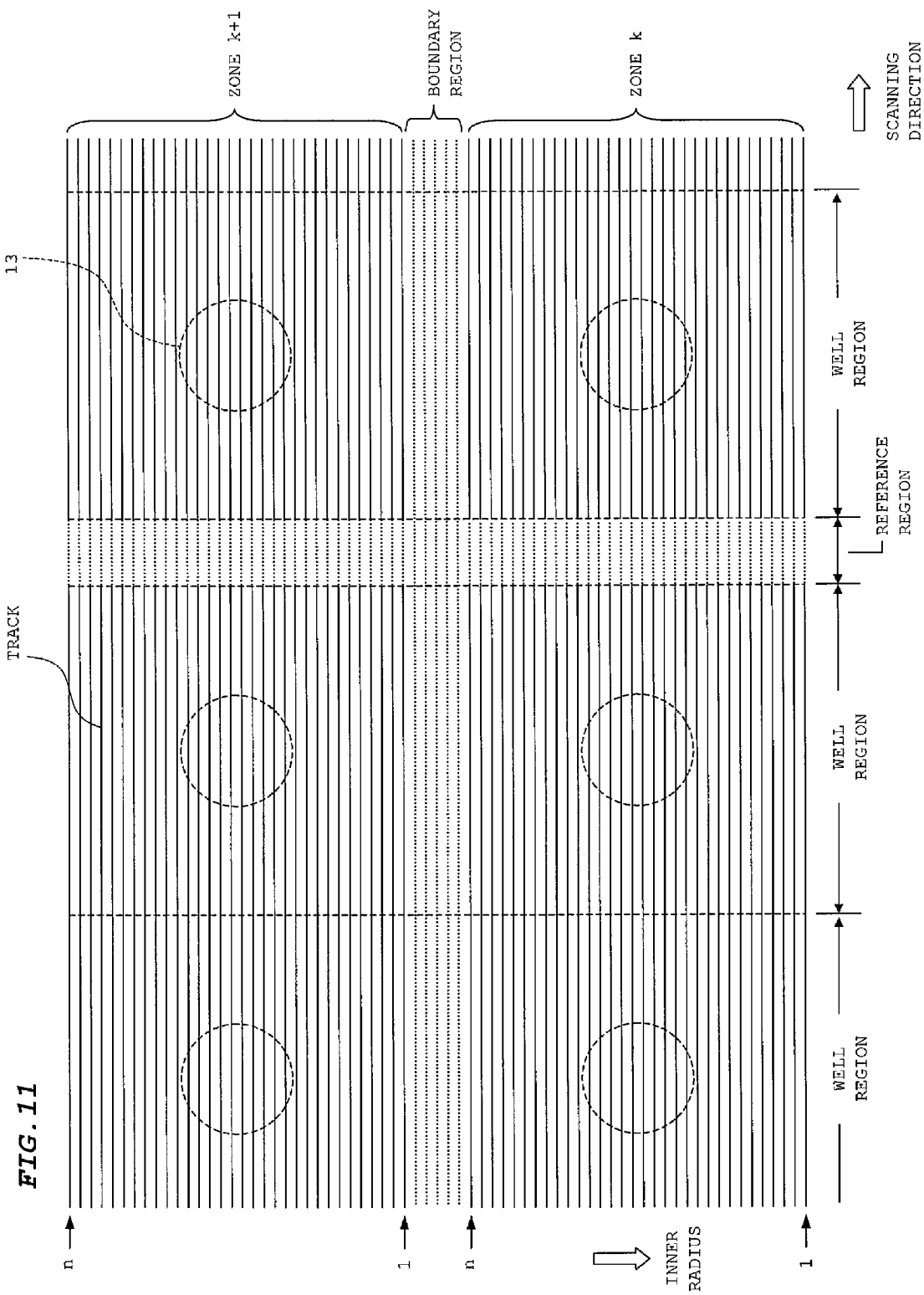
FIG. 11 is a diagram of the area allocation of a biosensor substrate according to modification 2.

FIG. 11 is a diagram of the configuration of a biosensor substrate 10 according to modification 2.

In the modification, a boundary region is provided between two zones adjacent in the radial direction. Tracks included in the boundary region are formed of pit strings similarly to the reference region. In the modification, this pit string is formed of a unique pattern different from the reference synchronization signal of the reference region. In the modification, the pit string of the boundary region does not hold special information.

FIG. 12 is a diagram of a data format set on the reference region. It is noted that FIG. 12 is a region near zone 1 disposed on the innermost radius.

As illustrated in FIG. 12, in the modification, the zone number is not held on the reference region. In the embodiment described above, the zone number held on the reference region is acquired, and a zone presently being scanned is identified. However, in the modification, the boundary region is scanned, the pit pattern unique to the boundary region is detected, and then it is detected that the scan position is entered to the next zone. In the boundary region, the length of a pit and the length of a space from this pit to the subsequent pit are twice the length of a pit and the length of a space in the reference region, for example. The number of tracks included in the boundary region in the radial direction is set to a few tracks (about five tracks) in order that the boundary region can be correctly detected.

As described above, the region on which the wells 13 are disposed is physically divided into a plurality of zones by the boundary region formed of pit strings.

In the modification, the reproduction RF signal (the SUM signal) is outputted from the signal operating circuit 201 to the controller 205 illustrated in FIG. 7 in order that the controller 205 can detect that the scan position is entered to the boundary region. The controller 205 monitors the reproduction RF signal, and detects that the scan position is entered to the boundary region based on the generation of signals on the reproduction RF signal, the singles in a pattern corresponding to the pit and the space on the boundary region.

Figure 13B:
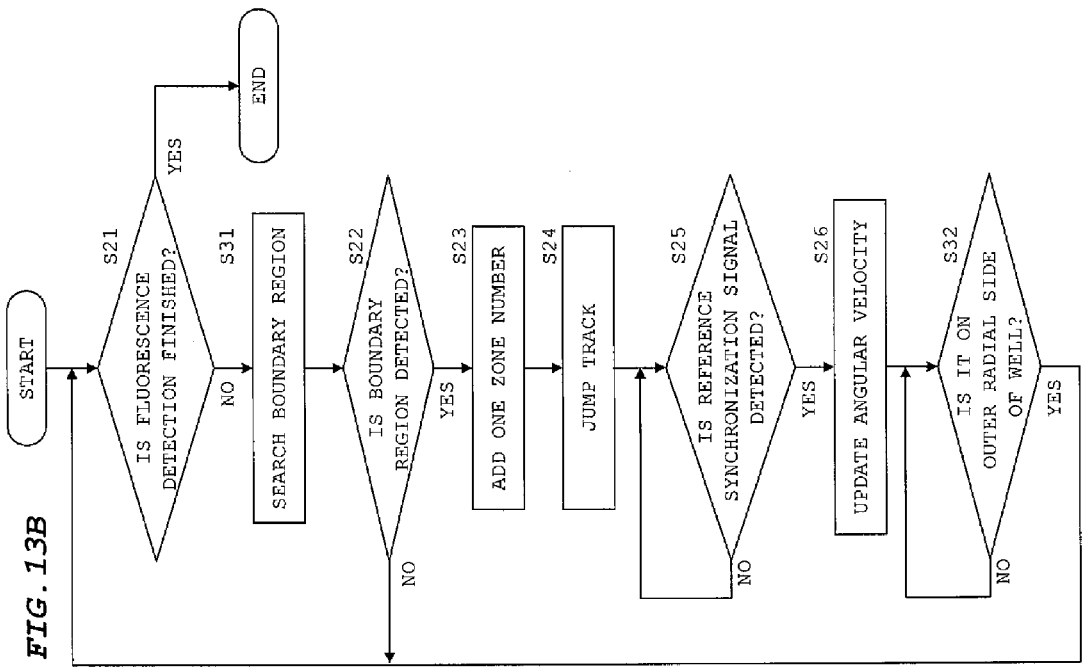
FIGS. 13A and 13B are flowcharts of the rotation control of the biosensor substrate according to modification 2.
Figure 13A:
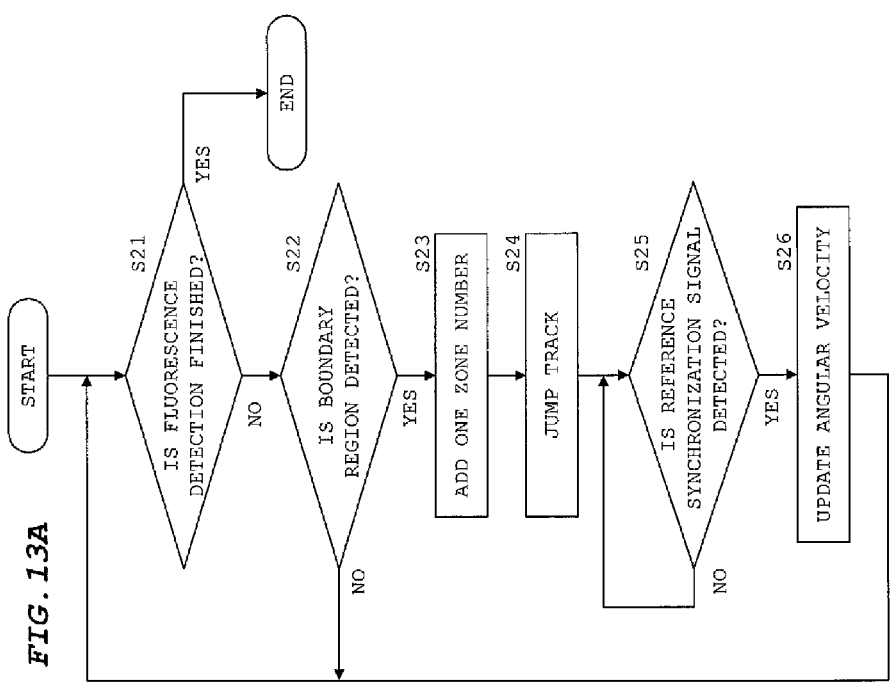

FIG. 13A is a flowchart of the update control of the angular velocity according to modification 2.

Until the fluorescence detection operation is finished (S21), the controller 205 monitors the reproduction RF signal inputted from the signal operating circuit 201, and determines whether the scan position of the excitation light beam is entered to the boundary region (S22). For example, when the biosensor substrate 10 is mounted on the fluorescence detector 1, the biosensor substrate 10 is rotated at a predetermined angular velocity, and the management zone illustrated in FIG. 12 is read. After that, the excitation light beam follows the track, and the scan position of the excitation light beam is entered to the boundary region disposed on the inner radial side of zone 1. Thus, the scan position is entered to the boundary region, and the controller 205 detects a pattern unique to the boundary region on the reproduction RF signal inputted from the signal operating circuit 201, and determines that the scan position is entered to the first boundary region (S22: YES).

When the controller 205 determines that the scan position is entered to the boundary region (S22: YES), the controller 205 increments the zone number by one, and outputs a track jump instruction to the servo circuit 202 that the scan position is passed through the boundary region and jumped to a zone on the outer radius side. For example, as described above, in the case where after information on the management zone is read, the scan position of the excitation light beam is first entered to a boundary region (a boundary region disposed on the inner radial side of zone 1) (S22: YES), the controller 205 increments the zone number held for the angular velocity control from zero to one (S23), and outputs an instruction to the servo circuit 202 to jump the scan position in the outer radial direction in the width corresponding to the number of tracks on the boundary region so that scan position jumps from the boundary region to zone 1 (S24). The servo circuit 202 jumps the scan position of the excitation light beam in the outer radial direction by a method similar to the existing optical disk techniques.

Thus, after the track jump is performed, the controller 205 determines whether the excitation light beam is scanned over the reference synchronization signal in the reference region (S25). The controller 205 monitors the reproduction RF signal, and detects that the excitation light beam is scanned over the reference synchronization signal based on the generation of signals on the reproduction RF signal, the signals in a pattern corresponding to the pit and the space on the reference synchronization signal. After detecting the reference synchronization signal (S25: YES), the controller 205 acquires the angular velocity corresponding to the zone number acquired in S23 from the angular velocity table 205a, and updates the angular velocity of the biosensor substrate 10 to the acquired angular velocity (S26).

After that, the controller 205 returns the process to S21, and waits for the arrival of the subsequent boundary region until the fluorescence detection operation is finished (S22). When the scan position is entered to the subsequent boundary region (S22: YES), the controller 205 performs the processes after S23. The controller 205 repeats the similar processes until it is determined that the fluorescence detection operation is finished in S21. The determination whether the fluorescence detection operation is finished is performed similarly to the embodiment described above. When the fluorescence detection operation is finished (S21: YES), the controller 205 ends the update process of the angular velocity.

Also in the modification, the effect similar to the effect in the embodiment described above can be exerted.

It is noted that in the flowchart in FIG. 13A, the excitation light beam is continuously scanned over the track as it is until the scan position of the excitation light beam is entered to the boundary region. However, it may be fine that a process of searching the subsequent boundary region is further performed in response to the end of scanning the well 13.

FIG. 13B is a flowchart of the update process of the angular velocity in this case. In the flowchart in FIG. 13B, S31 and S32 are additionally provided to the flowchart in FIG. 13A.

In S31, the boundary region is searched, and in S32, it is determined whether the scan position of the excitation light beam goes to the outer radial side of the well 13 in the zone.

In the search process in S31, for example, the scan position of the excitation light beam is jumped on the outer radial side by a few tracks, and at the scan position after the jump, it is determined whether a pattern unique to the boundary region appears on the reproduction RF signal. The process in S31 is repeatedly performed until a pattern unique to the boundary region appears on the reproduction RF signal. It is detected that a pattern unique to the boundary region appears on the reproduction RF signal, and it is determined in S22 that the scan position of the excitation light beam is entered to the boundary region (S22: YES).

The determination in S32 is performed based on an event that for example, the state in which the signal level of the reproduction RF signal is changed while the biosensor substrate 10 is making one turn is shifted to the state in which the signal level of the reproduction RF signal is not changed while the biosensor substrate 10 is making one turn. In addition to the reflected excitation light beam reflected on the reflective film 14 illustrated in FIG. 1C, the excitation light beam, that is transmitted through the reflective film 14, reflected on the well the bottom portion 13a, and again transmitted through the reflective film 14 (a stray light beam), is also entered to the photodetector 109 illustrated in FIG. 7. Therefore, in the period in which the excitation light beam is scanned over the position corresponding to the well 13, the light receiving quantity of the photodetector 109 is increased by the amount of this stray light beam, and the signal level of the reproduction RF signal is raised.

In the case where the scan trace of the excitation light beam is applied to the well 13, a change corresponding to the stray light beam is taken palace on the signal level of the reproduction RF signal while the biosensor substrate 10 is making one turn. When the scan trace of the excitation light beam goes to the region on the outer side beyond the well 13, the stray light beam is not entered to the photodetector 109, and the signal level of the reproduction RF signal is not changed even though the biosensor substrate 10 makes one turn. Therefore, it can be detected that the scan position of the excitation light beam goes to the outer radial side beyond the well 13 based on an event that the state in which the signal level of the reproduction RF signal is changed while the biosensor substrate 10 is making one turn is shifted to the state in which the signal level of the reproduction RF signal is not changed while the biosensor substrate 10 is making one turn.

In the flowchart in FIG. 13B, when the management zone on the biosensor substrate 10 is read, the boundary region disposed on the innermost radius is searched in S31 (S31). When the boundary region on the innermost radius is detected by this search (S32: YES), the processes after S23 are performed, and the angular velocity is updated similarly to FIG. 13A. When the angular velocity is updated (S26), the controller 205 determines whether the scan position of the excitation light beam goes to the region on the outer side beyond the well 13 (S32). When the scan position goes to the region on the outer side beyond the well 13 (S32: YES), the controller 205 determines whether the fluorescence detection operation is finished (S21). When the fluorescence detection operation is not finished (S21: NO), the boundary region on the further outer radial side is searched (S31).

According to the flowchart in FIG. 13B, when the scan position of the excitation light beam goes to the outer side beyond the well 13, the subsequent boundary region is searched, so that the test on the biosensor substrate 10 can be quickly finished as compared with the flowchart in FIG. 13A.

Figure 14B:
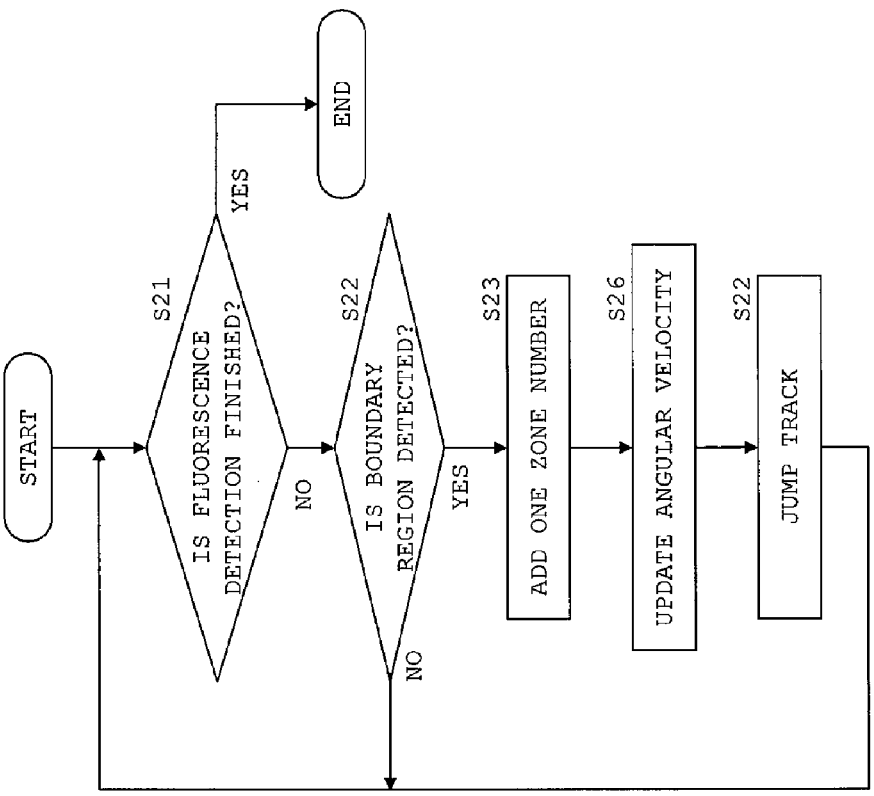
FIGS. 14A and 14B are a flowchart in the case where the rotation control of the biosensor substrate according to modification 2 is applied to rotation control according to the embodiment, and a flowchart of another rotation control according to modification 2, respectively.
Figure 14A:
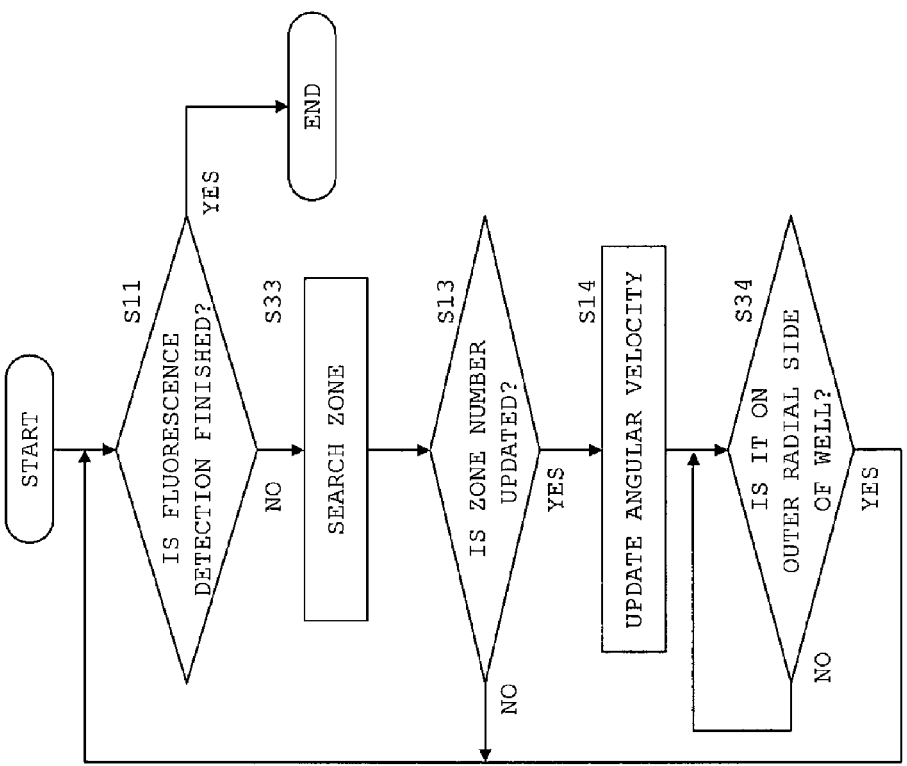

It is noted that the search process illustrated in FIG. 13B is also applicable to the flowchart in FIG. 8A in the embodiment. In this case, as illustrated in FIG. 14A, when the angular velocity is updated in the process in S14, it is determined whether the scan position of the excitation light beam goes to the region on the outer side beyond the well 13. When the scan position of the excitation light beam goes to the region on the outer side beyond the well 13, the process is forwarded to S11. When the fluorescence detection operation is not finished (S11: NO), the process is performed that the zone on the further outer radial side is searched (S33).

In the search process, the scan position of the excitation light beam is jumped on the outer radial side by a few tracks, and at the scan position after the jump, it is determined that a new zone number is acquired. The search process is repeatedly performed until a new zone number is acquired. When a new zone number is acquired, the determination in S13 is YES, and in S14, the angular velocity of the biosensor substrate 10 is updated to the angular velocity corresponding to a new zone number.

In the flowchart in FIG. 14A, the test on the biosensor substrate 10 can be quickly finished as compared with the flowchart in FIG. 8A.

It is noted that in FIGS. 13A and 13B, the scan position of the excitation light beam is entered to the zone on the outer side of the boundary region, and in accordance with the detection of the reference synchronization signal (S25: YES), the angular velocity is updated (S26). However, it may be fine that the angular velocity is updated accordance with the detection of the boundary region. In this case, the flowchart in FIG. 13A is altered as in FIG. 14B. In other words, when the boundary region is detected (S22: YES), the zone number is incremented by one (S23), and the angular velocity of the biosensor substrate 10 is updated to the angular velocity corresponding to the zone number after incremented (S26). After that, the scan position of the excitation light beam is jumped to tracks on the outer radius side, and the zone on the outer radial side is scanned. The flowchart in FIG. 13B is also similarly changeable.

<Modification 3>

In modification 2 described above, special information is not held on the tracks included in the boundary region. On the other hand, in modification 3, a zone number is held on the boundary region.

Figure 15:
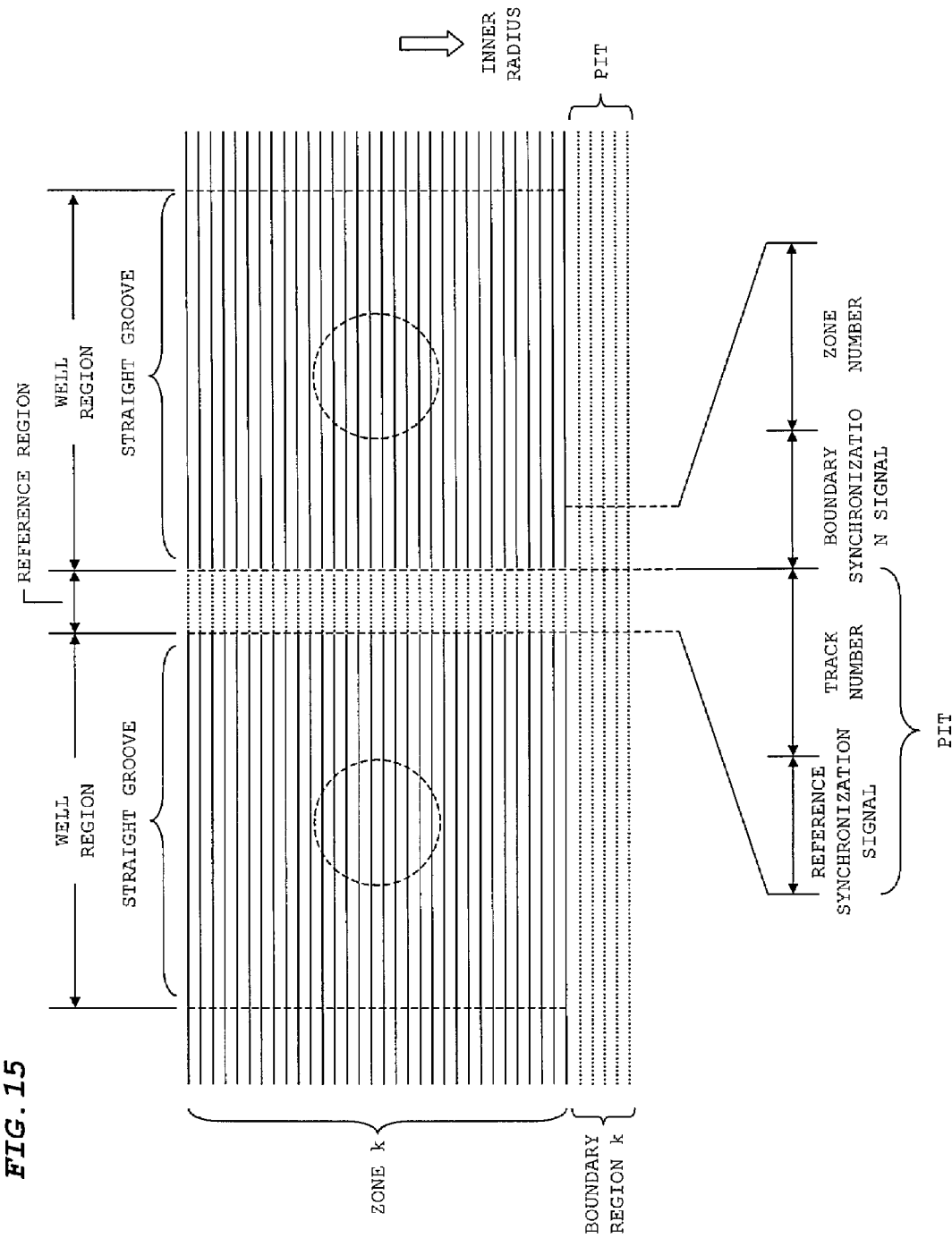
FIG. 15 is a diagram of data formats set on a reference region and a boundary region according to modification 3.

FIG. 15 is a diagram of the configuration of a biosensor substrate 10 according to modification 3 and data formats on the reference region and the boundary region.

As illustrated in FIG. 15, in modification 3, a boundary synchronization signal and a zone number are held on the tracks on a kth boundary region k from the inner radius side. The boundary synchronization signal is formed of a unique pattern of a pit and a space similarly to the case of modification 2 described above. The zone number is the zone number of the zone k on the outer side of the boundary region k, that is, the kth zone k from the inner radius side. On the tracks on the boundary region k, a set formed of the boundary synchronization signal and the zone number is repeatedly recorded across the entire period of the tracks. Moreover, instead of this, it may be fine that a set formed of the boundary synchronization signal and the zone number is recorded for one time or a few times on the track portion subsequent to the reference region, and other items of information are recorded on the section of the tracks after that, or a dot and a space are arranged in random patterns.

As described above, in the modification, the boundary region k formed of pit strings holds the zone number of a zone on the outer side of the boundary region k.

Figure 16A:
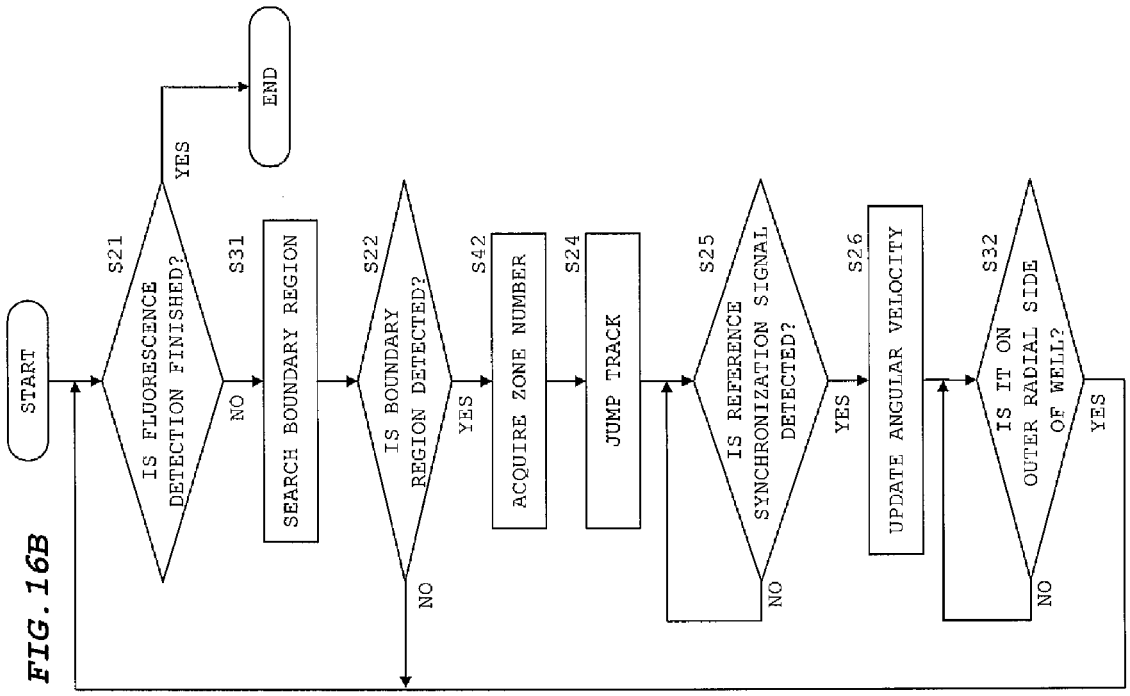
FIGS. 16A and 16B are flowcharts of another rotation control of a biosensor substrate according to modification 3.

FIG. 16A is a flowchart of the update process of the angular velocity according to modification 3. In the flowchart in FIG. 16A, S23 in the flowchart in FIG. 13A is replaced by S41, and the other steps are the same as in the flowchart in FIG. 13A.

When the boundary region is detected in S22 in FIG. 16A (S22: YES), a zone number is acquired from this boundary region (S41). A track jump is performed in S24, and after that, when the reference synchronization signal is detected (S25: YES), the angular velocity of the biosensor substrate 10 is updated to the angular velocity corresponding to the zone number acquired in S41 (S26).

Figure 16B:
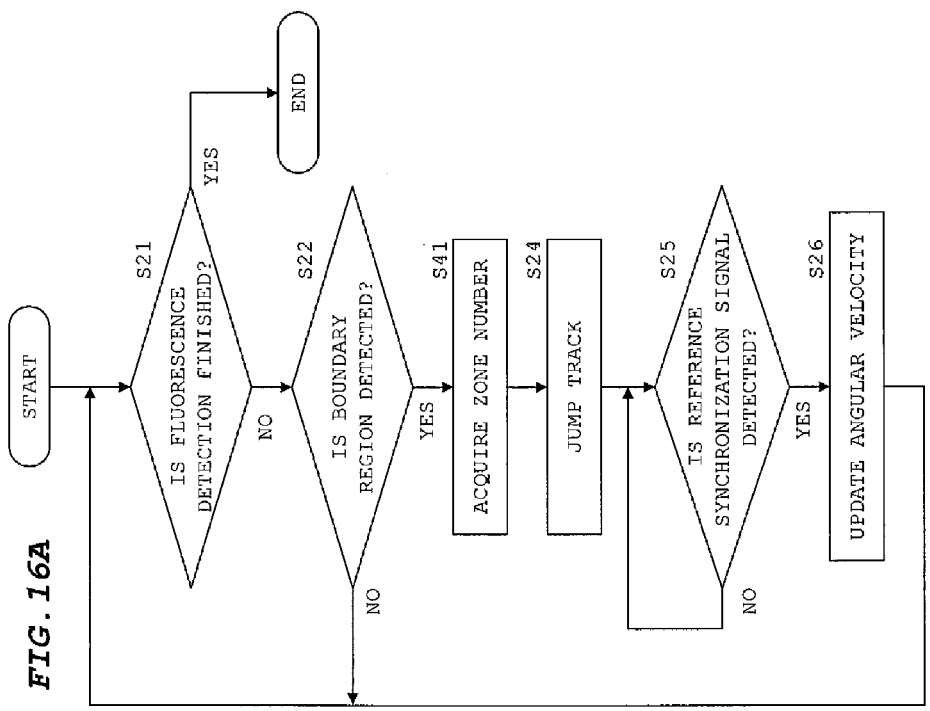

In FIG. 16B, S23 in the flowchart in FIG. 13B is replaced by S42. Also in this flowchart, when the boundary region is detected in S22 (S22: YES), a zone number is acquired from this boundary region (S42). A track jump is performed in S24, and after that, when the reference synchronization signal is detected (S25: YES), the angular velocity of the biosensor substrate 10 is updated to the angular velocity corresponding to the zone number acquired in S42 (S26).

Also in the modification, the effect similar to the effect in the embodiment described above can be exerted. Moreover, it may be fine that the flowcharts FIGS. 16A and 16B are altered so that the angular velocity is updated in accordance with an event that the scan position of the excitation light beam is entered to the boundary region similarly to FIG. 14B.

<Modification 4>

In the embodiment described above, a single angular velocity is set to one zone. However, it may be fine that a single angular velocity is set to a plurality of zones adjacent in the radial direction.

Figures 17A, 17B:
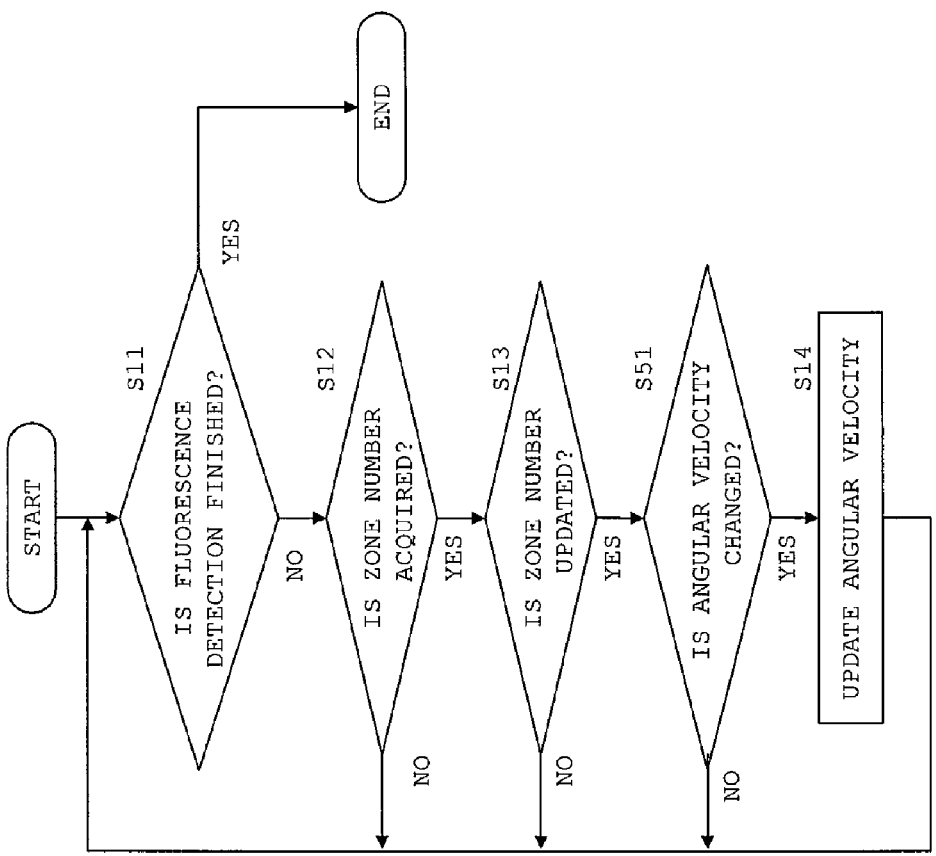
FIGS. 17A and 17B are a flowchart of the rotation control of a biosensor substrate according to modification 4 and a diagram of the configuration of an angular velocity control table held on a controller, respectively.

FIG. 17A is a flowchart of angular velocity update control in the case where a single angular velocity is set to two zones adjacent in the radial direction, and FIG. 17B is a diagram of the configuration of an angular velocity table 205a. In the flowchart in FIG. 17A, S51 is additionally provided to the flowchart in FIG. 8A. Moreover, as illustrated in FIG. 17B, in the angular velocity table 205a according to the modification, a single angular velocity is allocated to two zone numbers. Here, the angular velocity allocated to a set of two zone numbers is smaller than the angular velocity allocated to a set of two zone numbers one set on the inner radial side of this set. For example, the angular velocities of the individual sets are set in this manner that the linear velocity of the track on the innermost radius on the zone having a zone number on the inner radial side in a set of two zone numbers is the same as the linear velocity of the track on the innermost radius on the zone having a zone number on the inner radial side in another set of two zone numbers.

In the flowchart in FIG. 17A, when the controller 205 determines that the zone number acquired from the reference region this time is changed from the previously acquired zone number (S13: YES), the controller 205 acquires the angular velocity corresponding to the acquired zone number from the angular velocity table 205a, and determines whether the acquired angular velocity is different from the angular velocity presently set (S51). When the acquired angular velocity is different from the angular velocity presently set (S51: YES), the controller 205 updates the angular velocity of the biosensor substrate 10 to the angular velocity acquired this time (S14).

According to the modification, the angular velocity of the biosensor substrate 10 is maintained until the zone number is changed twice, so that the operation of changing the angular velocity can be made simpler than in the embodiment described above. Moreover, since a single angular velocity is set to two zones, the angular velocity to the zone on the outer radial side in these two zones is faster than in the embodiment described above, and as a result, the time necessary to scan the entire region of the biosensor substrate 10 can be shortened. However, on the other hand, in the modification, since the angular velocity to the zone on the outer radial side in these two zones is faster than in the embodiment described above, the light beam quantity of an excitation light beam applied to a specimen in scanning the zone on the outer radial side is decreased more than in the embodiment described above. Therefore, in the case where fluorescence is sufficiently emitted from the specimen even though the light beam quantity of the excitation light beam applied to the specimen is decreased as described above, it is desirable to allocate a single angular velocity to two adjacent zones as in the modification. The number of zones to which a single angular velocity is allocated can be appropriately set in a range in which a decrease in the light beam quantity of the excitation light beam applied to the specimen is allowed.

<Modification 5>

Figure 18:
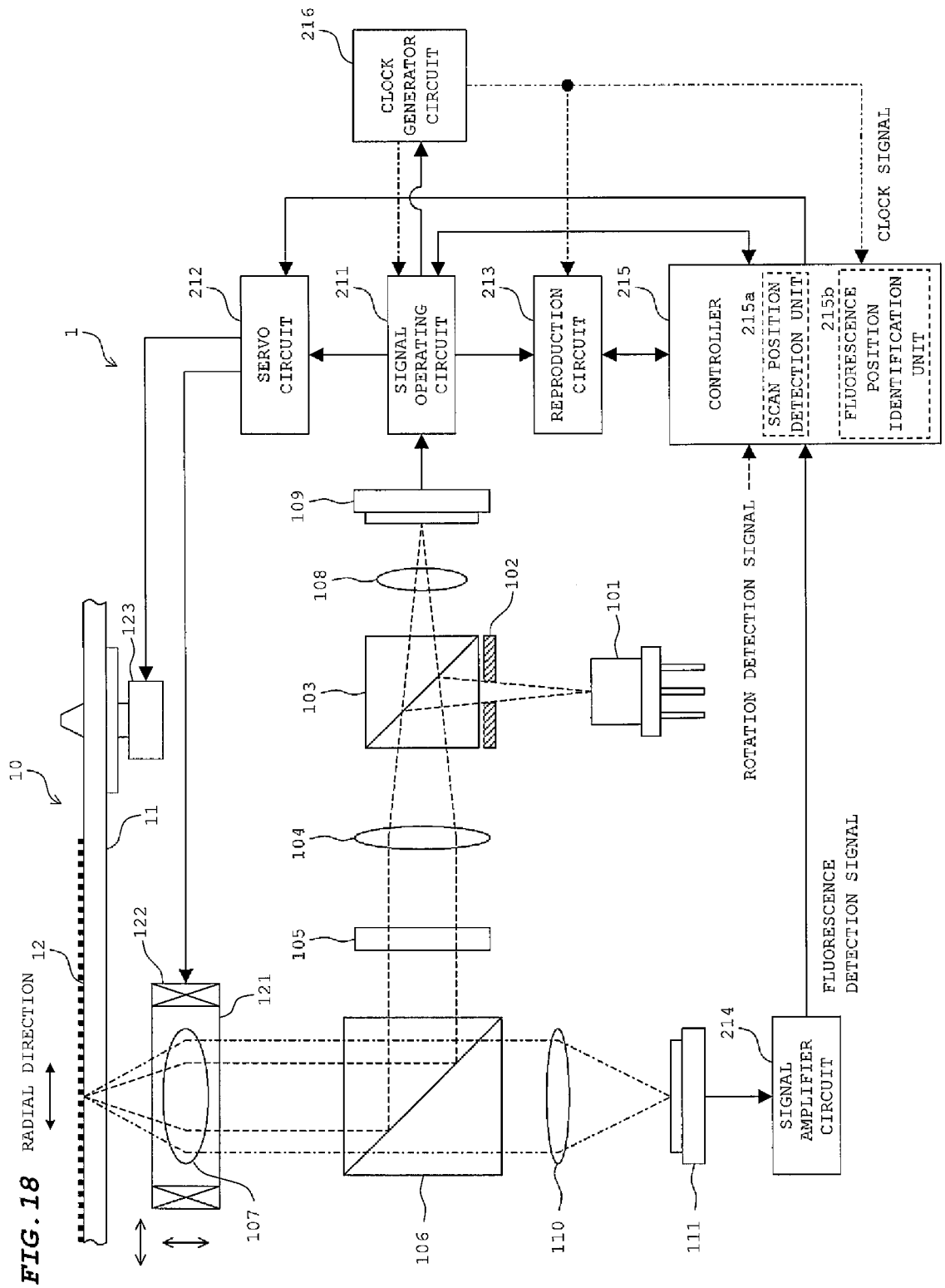
FIG. 18 is a diagram of the configuration of a fluorescence detector according to modification 5.

FIG. 18 is a diagram of the configuration of a fluorescence detector 1 according to this modification.

It is noted that the biosensor substrate 10 illustrated in modification 1 is used for measurement using the fluorescence detector 1 according to the modification. The biosensor substrate 10 is provided with the address region separately from the reference region, and the well synchronization signal, the track number, and the well number are held on the address region (see FIG. 10).

The optical system of the fluorescence detector 1 according to the modification includes a semiconductor laser 101, an aperture 102, a polarization beam splitter (PBS) 103, a collimator lens 104, a quarter-wave plate 105, a dichroic prism 106, an objective lens 107, an anamorphic lens 108, a photodetector 109, a condenser lens 110, and a fluorescence device 111, similarly to the embodiment described above. Moreover, the fluorescence detector 1 includes a holder 121, an objective lens actuator 122, and a rotating device 123, similarly to the embodiment described above. Since the configurations of these components are already described in the embodiment, the description here is omitted.

The fluorescence detector 1 further includes a signal operating circuit 211, a servo circuit 212, a reproduction circuit 213, a signal amplifier circuit 214, a controller 215, and a clock generator circuit 216.

The signal operating circuit 211 generates a focus error signal FE, a tracking error signals TE1 and TE2, and a reproduction RF signal from the detection signal of the photodetector 109. These signals will be described later with reference to FIG. 19.

The servo circuit 212 controls the driving of the objective lens actuator 122 using the focus error signal FE and the tracking error signal TE1 outputted from the signal operating circuit 201. Moreover, the servo circuit 212 controls the moving of a housing in which the optical system of the fluorescence detector 1, the holder 121, and the objective lens actuator 122 are disposed. Furthermore, the servo circuit 212 controls the rotating device 123 in such a manner that the biosensor substrate 10 is rotated at a constant angular velocity in the individual zones based on the rotation detection signal outputted from the rotating device 123 every time when the biosensor substrate 10 makes one turn. In the control, the update control of the angular velocity illustrated in FIG. 8A is performed, and the angular velocity to the zone is updated by the controller 215 in such a manner that the angular velocity to the zone is more decreased as the position at which the zone is disposed goes toward the outer radial side of the biosensor substrate 10. It is noted that the rotating device 123 also outputs the rotation detection signal to the controller 215 in addition to the servo circuit 212.

The reproduction circuit 213 demodulates the reproduction RF signal outputted from the signal operating circuit 211, and generates reproduction data. The reproduction data to be demodulated is the zone number, the track number, and the well number held on the reference region and the address region illustrated in FIG. 10. The reproduction circuit 213 outputs the demodulated reproduction data to the controller 215. The signal amplifier circuit 214 amplifies the detection signal of the fluorescence device 111 (the fluorescence detection signal), and outputs the signal to the controller 205.

The controller 215 includes a CPU and a memory, and controls the units of the fluorescence detector 1 in addition to the signal operating circuit 211, the servo circuit 212, and the reproduction circuit 213 in accordance with programs stored on the memory. Moreover, the controller 215 includes a function as a scan position detection unit 215a and a fluorescence position identification unit 215b in accordance with the programs stored on the memory. It is noted that an angular velocity table (not shown) is held on the controller 215 similarly to the embodiment described above.

The scan position detection unit 215a detects the scan position of the excitation light beam at the track portions included in the well region based on a signal (a reproduction RF signal) outputted from the signal operating circuit 211 and a signal (a clock signal) outputted from the clock generator circuit 216. Moreover, the fluorescence position identification unit 215b determines the position of the well 13, in which fluorescence is detected, on the biosensor substrate 10 based on reproduction data (a zone number and a well number) outputted from the reproduction circuit 213 and a signal (a fluorescence detection signal) outputted from the signal amplifier circuit 214, and holds the zone number and the well number corresponding to the well 13 in which fluorescence is detected on an internal memory. Furthermore, the fluorescence position identification unit 215b identifies the position at which fluorescence is emitted in the well 13 based on reproduction data (the track number) outputted from the reproduction circuit 213, a signal (a fluorescence detection signal) outputted from the signal amplifier circuit 214, and the scan position detected by the scan position detection unit 215a, and holds them on an internal memory.

In addition, the controller 215 determines whether the scan position deviates from a target track when the excitation light beam is scanned over the straight groove based on the tracking error signal TE2 outputted from the signal operating circuit 211. When the controller 215 determines that the scan position deviates from the target track, the controller 215 controls the servo circuit 212 to again scan the same track with the excitation light beam.

The clock generator circuit 216 generates clocks at a predetermined frequency in synchronization with the reproduction RF signal based on the reproduction RF signal inputted from the signal operating circuit 211, and supplies the generated clocks to the circuits.

FIG. 19 is a diagram of the circuit configuration of the signal operating circuit 211.

The photodetector 109 includes a quadrant sensor that receives a reflected excitation light beam on the light receiving surface as described above. Sensors at the upper left, at the upper right, at the lower right, and at the lower left consisting the quadrant sensor output detection signals S1 to S4, respectively, based on the beam spot of the received reflected excitation light beam. It is noted that on the light receiving surface of the photodetector 109 in FIG. 18, the direction corresponding to the radial direction of the disk is the lateral direction. Moreover, the focus error signal FE and the tracking error signal TE are generated in accordance with the astigmatism method and the differential phase detection method (DPD method) used for existing optical disk apparatuses.

The signal operating circuit 211 includes adders 301 to 304 and 306, a subtractor 305, a phase difference detection circuit 311, a control circuit 312, a sample-and-hold circuit 313, and lowpass filters (LPFs) 314 and 315. The adder 301 outputs a signal that the detection signals S1 and S3 are added to the subtractor 305 and the phase difference detection circuit 311, and the adder 302 outputs a signal that the detection signals S2 and S4 are added to the subtractor 305 and the phase difference detection circuit 311. The adder 303 outputs a signal that the detection signals S1 and S4 are added to the adder 306, and the adder 304 outputs a signal that the detection signals S2 and S3 are added to the adder 306.

The subtractor 305 subtracts the output signals of the adders 301 and 302, and outputs the focus error signal FE. The adder 306 adds the output signals of the adders 303 and 304, and outputs the reproduction RF signal (the SUM signal). The phase difference detection circuit 311 generates the tracking error signal TE based on the phase difference between the output signals of the adders 301 and 302. When the position of the focal point of the objective lens 107 is positioned on the reflection plane 11a, the beam spot on the quadrant sensor of the photodetector 109 is a circle of least confusion, and the value of the focus error signal FE is zero. Moreover, when the position of the focal point of the objective lens 107 is positioned right above the track on the reflection plane 11a, the phase of the beam spot applied to two sensors on the left side of the quadrant sensor is equal to the phase of the beam spot applied to two sensors on the right side of the quadrant sensor, and the value of the tracking error signal TE is zero.

The control circuit 312 turns the sample-and-hold circuit 313 into an open state or a hold (retention) state based on the reproduction RF signal and the clock signal. When the sample-and-hold circuit 313 is controlled to open the signal by the control circuit 312, the sample-and-hold circuit 313 outputs the tracking error signal TE outputted from the phase difference detection circuit 311 to the LPF 314 on the subsequent stage. Moreover, when the sample-and-hold circuit 313 is controlled to hold (retain) a signal by the control circuit 312, the sample-and-hold circuit 313 continuously outputs the tracking error signal TE outputted from the phase difference detection circuit 311 immediately before holding (retention) control to the LPF 314 on the subsequent stage until the sample-and-hold circuit 313 is controlled to open the signal after that. The LPF 314 removes the high frequency component of the signal outputted from the sample-and-hold circuit 313, and outputs the tracking error signal TE1. The LPF 315 removes the high frequency component of the tracking error signal TE outputted from the phase difference detection circuit 311, and outputs the tracking error signal TE2.

Figure 20A:
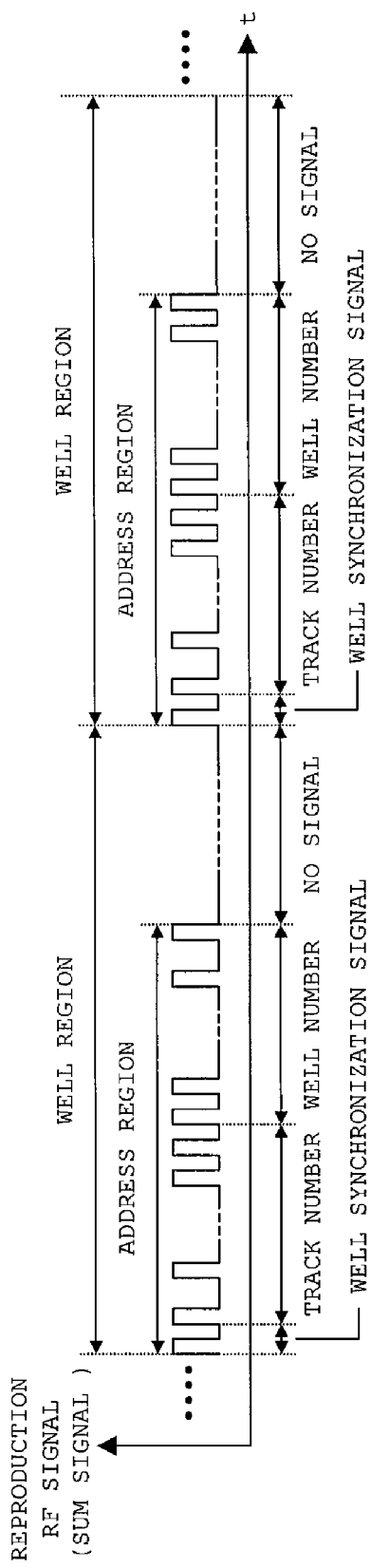
FIGS. 20A and 20B are schematic diagrams of a reproduction RF signal according to modification 5.
Figure 20B:
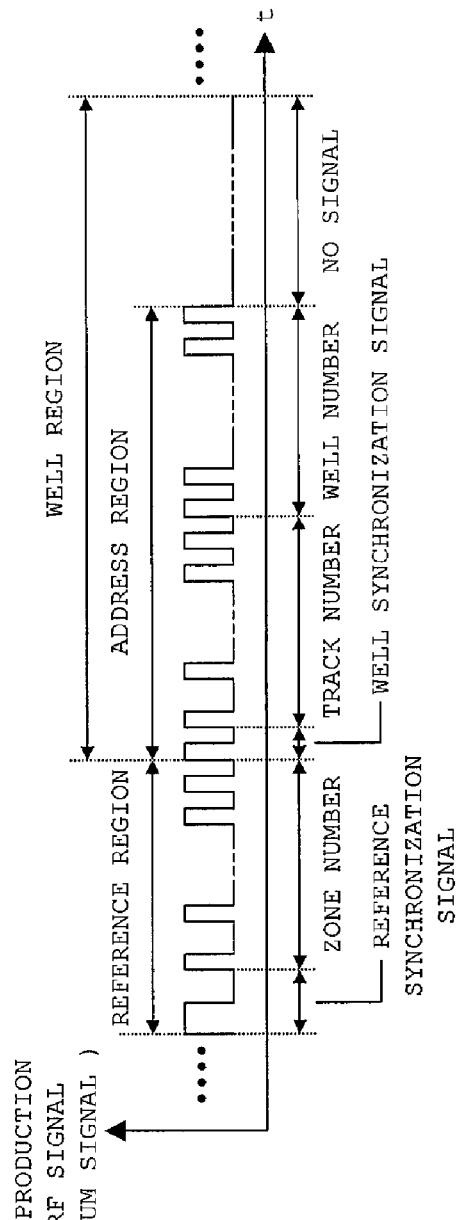

FIGS. 20A and 20B are schematic diagrams of the reproduction RF signal outputted from the adder 306 in FIG. 19.

Referring to FIG. 20A, in the case where the excitation light beam is scanned over the pit strings on the address region illustrated in FIG. 10, waveforms corresponding to the well synchronization signal, the track number, and the well number in turn appear on the reproduction RF signal. In the modification, the well synchronization signal is formed of one TM (a pit mark for a duration 1 T) and one TS (a space for the duration 1 T). It is noted that it is fine that the physical length of one T is in a reproducible range with respect to the number of revolutions when data is reproduced or in a band width of the transmission circuit. In the case where the excitation light beam is scanned over the straight grooves on the well region, the waveforms corresponding to the pit do not appear on the reproduction RF signal.

Referring to FIG. 20B, in the case where the excitation light beam is scanned over the pit strings on the reference region illustrated in FIG. 10, waveforms corresponding to the reference synchronization signal and the zone number in turn appear on the reproduction RF signal. The reference synchronization signal according to the embodiment is formed of two TMs and two TSs.

Meanwhile, in the signal operating circuit 211 illustrated in FIG. 19, the tracking error signal TE1 is generated based on the phase difference between the signals from the sensors configuring the quadrant sensor of the photodetector 109 as described above. The generated tracking error signal TE1 is a signal that reflects how the excitation light beam is applied to the tracks. Therefore, in order to generate the tracking error signal TE1 of excellence, it is demanded that light disturbance beams other than the reflected excitation light beam be not entered to the quadrant sensor as much as possible. When the light disturbance beam is entered to the quadrant sensor, the tracking error signal TE1 is degraded, and tracking servo becomes unstable.

However, as illustrated in FIG. 1D, the biosensor substrate 10 is configured such that a part of the excitation light beam is transmitted through the reflection plane 11a. In this case, a part of the excitation light beam transmitted through the reflection plane 11a is reflected on the bottom portion 13a, and the reflected excitation light beam is again transmitted through the reflection plane 11a, and guided to the photodetector 109. Therefore, the excitation light beam reflected on the bottom portion 13a (a stray light beam) is also entered to the photodetector 109, in addition to the reflected excitation light beam used for tracking servo.

In this case, when this stray light beam is unequally entered to the sensors configuring the quadrant sensor, the tracking error signal TE1 is degraded. More specifically, when the excitation light beam is entered to the boundary portion of the bottom portion 13a, the excitation light beam is scattered or the reflection direction is changed, and the stray light beam is easily entered to the sensors in an unequal state. Thus, when the tracking error signal TE1 is greatly degraded, tracking servo excessively becomes unstable, and it is likely that the scan position of the excitation light beam deviates from the track targeted for scanning.

More specifically, in the biosensor substrate 10, the reflectance of the reflective film 14 to the excitation light beam is set low in order to guide a much greater quantity of the excitation light beam to the specimen. Therefore, the light beam quantity of the excitation light beam to be a stray light beam after guided to the bottom portion 13a is also large, and the light beam quantity of the stray light beam entered to the photodetector 109 is relatively greater than the light beam quantity of the reflected excitation light beam accordingly. Thus, such a phenomenon is easily taken place that the influence of tracking servo caused due to the stray light beam becomes large and tracking servo excessively becomes unstable due to the stray light beam.

Therefore, in the modification, a scheme to avoid this phenomenon and to stabilize tracking servo is provided. More specifically, in the period in which the excitation light beam is scanned over the track portion corresponding to the well 13, the tracking error signal used for tracking servo is held (retained) to the value immediately before, and it is aimed to stabilize tracking servo. In the following, this control will be described.

Figure 21:
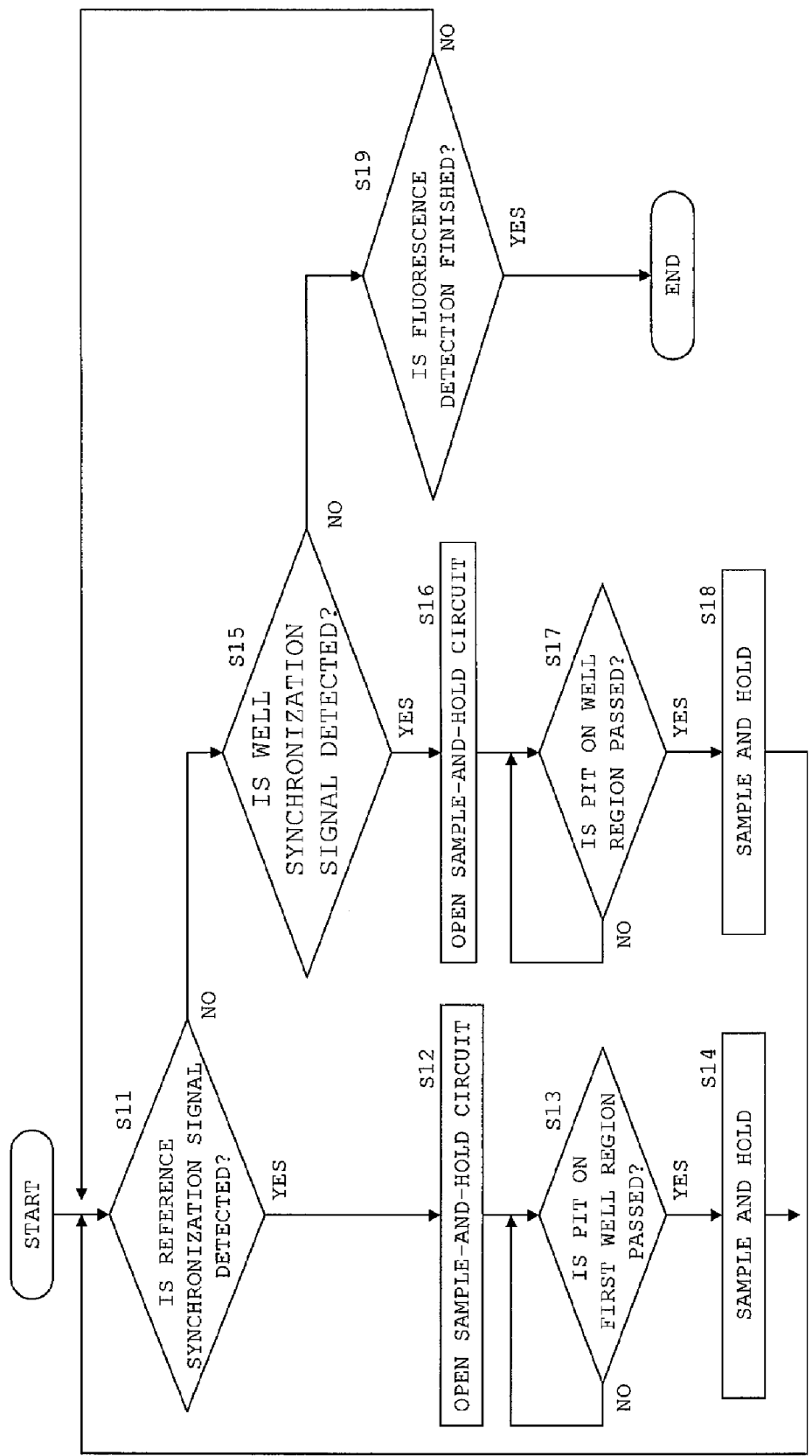
FIG. 21 is a flowchart of processes performed by a control circuit according to modification 5.

FIG. 21 is a flowchart of processes performed by the control circuit 312.

The control circuit 312 detects the reference synchronization signal and the well synchronization signal included in the reproduction RF signal, and performs processes in accordance with the detected synchronization signals. It is noted that the sample-and-hold circuit 313 is opened in advance when the fluorescence detector 1 is started.

It is noted that the control circuit 312 detects the synchronization signals based on an event that unique waveform patterns corresponding to the reference synchronization signal and the well synchronization signal appear on the reproduction RF signal (see FIGS. 20A and 20B).

In other words, as illustrated in FIG. 20A, the well synchronization signal appears on the reproduction RF signal subsequently to the period in which no waveforms appear. The control circuit 312 detects the well synchronization signal by detecting a waveform that one TM and one TS are continued subsequently to the period in which no waveforms appear. Moreover, as illustrated in FIG. 20B, the reference synchronization signal appears on the reproduction RF signal subsequently to the period in which no waveforms appear. The control circuit 312 detects the reference synchronization signal by detecting a waveform that two TMs and two TSs are continued subsequently to the period in which no waveforms appear.

It is noted that in the well region immediately after the reference region, since a waveform exists at the tail of the reference region as illustrated in FIG. 20B, the waveform of at the tail and the waveform of the well synchronization signal are mixed, and thus it is not enabled to detect the well synchronization signal formed of one TM and one TS. Therefore, the control circuit 312 controls the sample-and-hold circuit 313 on the well region immediately after the reference region based on the reference synchronization signal included in the reference region.

When the control circuit 312 detects the reference synchronization signal (S11: YES), the control circuit 312 opens the sample-and-hold circuit 313 (S12), and after that, the control circuit 312 keeps the sample-and-hold circuit 313 in the open state in the period until the scan position is passed through the pit strings (the address region) on the first well region (S13).

It is noted that in FIG. 20B, the period from the zone number to the well number is determined in advance. After detecting the reference synchronization signal, the control circuit 312 determines that the scan position is passed through the pit strings on the first well region based on a lapse of this period. For example, in accordance with the detection of the reference synchronization signal, the control circuit 312 starts to count clock signals inputted from the clock generator circuit 206, and determines that the timing at which the counted value reaches a value corresponding to the period from the zone number to the well number is the timing at which the scan position is passed through the pit strings on the first well region, that is, the timing at which the scan position approaches the straight grooves on the first well 13. Alternatively, it may be fine that instead of this method, the control circuit 312 determines the timing at which the scan position is passed through the pit strings on the first well region based on the elapsed time after detecting the reference synchronization signal, or it may be fine that the control circuit 312 determines that the scan position is passed through the pit strings on the first well region based on an event that a waveform is gone from the reproduction RF signal after detecting the reference synchronization signal.

Again referring to FIG. 21, when the scan position is passed through the pit strings on the first well region (S13: YES), the control circuit 312 sets the sample-and-hold circuit 313 in the hold (retention) state (S14).

Subsequently, when the control circuit 312 detects the well synchronization signal (S11: NO, S15: YES), the control circuit 312 opens the sample-and-hold circuit 313 (S16), and after that, the control circuit 312 keeps the sample-and-hold circuit 313 in the open state in the period until the scan position is passed through the pit strings on the well region (S17). When the scan position is passed through the pit strings on the well region (S17: YES), the control circuit 312 sets the sample-and-hold circuit 313 in the hold (retention) state (S18). Thus, for example, when the scan position is passed through the straight grooves on the first well region and approaches the well synchronization signal on the second well region, the sample-and-hold circuit 313 is opened, and general tracking servo is performed. When the scan position is passed through the pit strings on the second well region, the sample-and-hold circuit 313 is turned into the hold (retention) state, and tracking servo is performed based on the tracking error signal TE1 immediately before. After that, the control is repeatedly performed until the reference synchronization signal is detected.

In the case where the control circuit 312 does not detect any of the reference synchronization signal and the well synchronization signal (S11: NO and S15: NO), the control circuit 312 returns the process to S11, and continues the detection of the synchronization signals (S19) as long as the fluorescence detector 1 instructs the end of the fluorescence detection operation.

Figure 22A:
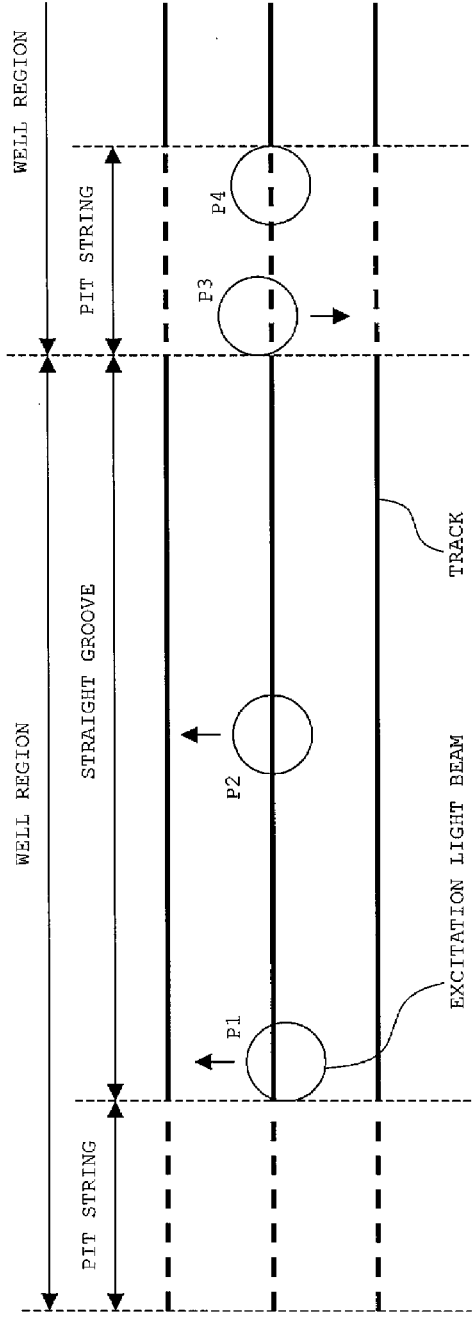
FIGS. 22A and 22B are schematic diagrams of the motion of an excitation light beam in the case where a sample-and-hold circuit according to modification 5 is controlled.
Figure 22B:
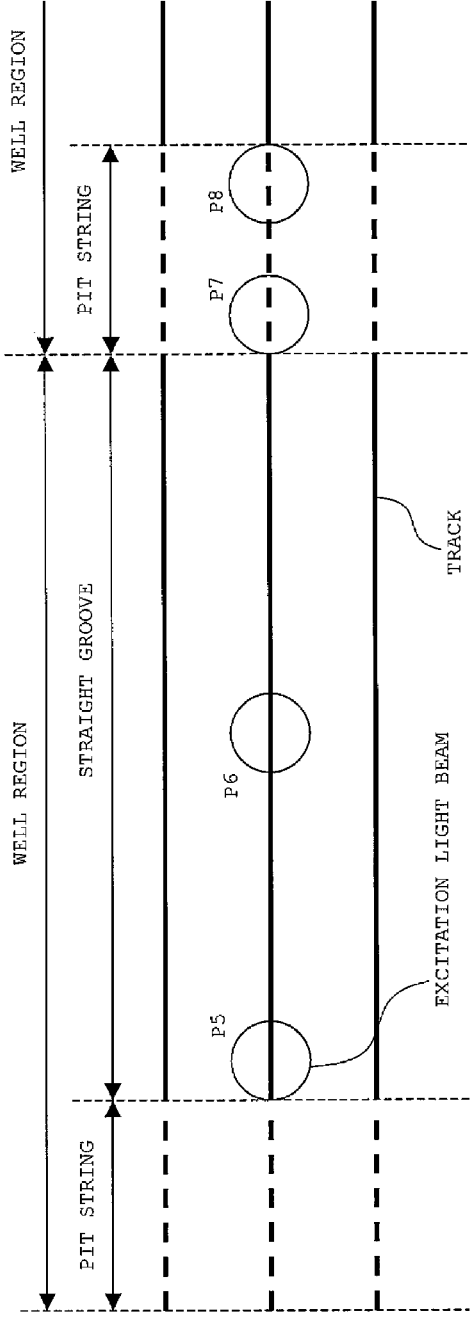

FIGS. 22A and 22B are schematic diagrams of the motion of the excitation light beam in the case where the sample-and-hold circuit 313 is controlled in accordance with the flowchart in FIG. 21.

For example, as illustrated in FIG. 22A, suppose that the excitation light beam is located at position P1 and the excitation light beam is displaced to the track in the downward direction at the timing at which the scan position of the excitation light beam is passed through the pit strings on the well region (the address region). In this case, when the tracking error signal TE1 has a value expressing a track displacement in the downward direction, the servo circuit 212 controls the position of the excitation light beam to be displaced upward based on the tracking error signal TE1. In the flowchart in FIG. 21, since the tracking error signal TE1 is held (retained) in the period in which the excitation light beam is scanned over the straight groove, control is performed to displace the position of the excitation light beam upward during the period. Therefore, the excitation light beam is moved further upward through position P2 as scanning proceeds, and positioned at position P3 at the timing at which the excitation light beam is entered to the pit strings on the subsequent well region. At this timing, the sample-and-hold circuit 313 is opened, and control based on the general tracking error signal TE1 is performed. Thus, the excitation light beam is moved downward, and positioned at position P4.

It is noted that as illustrated in FIG. 22B, in the case where the excitation light beam is located at position P5 that is an on track position and the value of the tracking error signal TE1 is nearly zero at the timing at which the scan position of the excitation light beam is passed through the pit strings on the well region, the servo circuit 212 controls the excitation light beam to be scarcely changed. Therefore, the excitation light beam goes from position P6 to position P7 as the excitation light beam is scarcely displaced off the track even though scanning proceeds. After that, the excitation light beam goes to position P8 as the excitation light beam remains nearly on the track even in the period in which the excitation light beam is scanned over the pit strings.

As described above, in control according to the flowchart in FIG. 21, even though the tracking error signal TE1 is controlled to be held (retained) in the period in which the excitation light beam is scanned over the straight groove, the excitation light beam can be scanned nearly along the track, and the excitation light beam can be correctly applied to the specimen in the well 13. However, since general tracking control is not performed in the period in which the excitation light beam is scanned over the straight grooves, it is likely that the scan position of the excitation light beam deviates from the track targeted for scanning because of some cause. In order to cope with this problem, in the embodiment, the following control is performed.

Figure 23A:
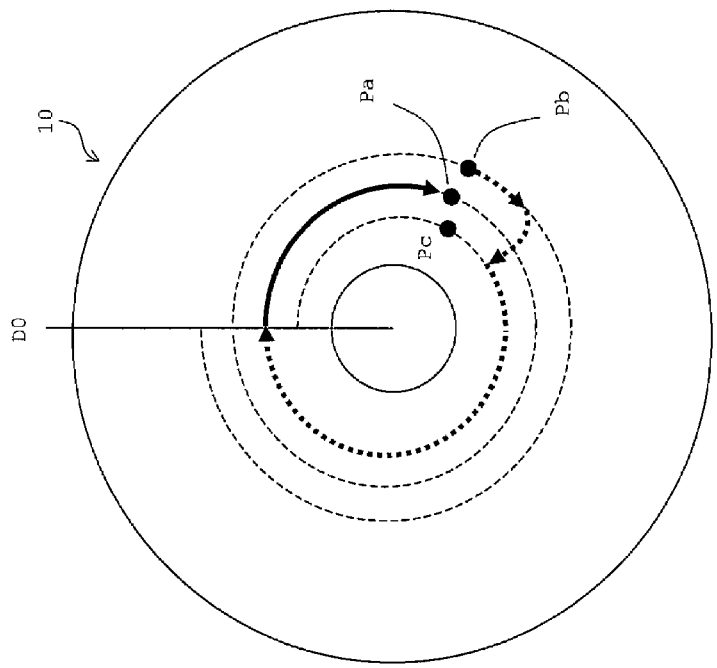
FIGS. 23A and 23B are a flowchart of control according to modification 5 in the case the scan position of an excitation light beam deviates from a scan target track and a schematic diagram of an exemplary control operation, respectively.

FIG. 23A is a flowchart of control when the scan position of the excitation light beam deviates from a scan target track while scanning the excitation light beam over the straight grooves.

The controller 215 monitors the tracking error signal TE2 outputted from the LPF 315 illustrated in FIG. 19, and determines whether the scan position of the excitation light beam deviates from the scan target track (S31). As illustrated in FIG. 19, the LPF 315 continuously outputs the tracking error signal TE2 while scanning the excitation light beam over the straight grooves, similarly to the excitation light beam being scanned over the pit strings. The controller 215 determines that the scan position of the excitation light beam deviates from the scan target track based on the change in the tracking error signal TE2.

For example, it is determined that the scan position of the excitation light beam deviates from the scan target track when the absolute value of the tracking error signal TE2 exceeds a predetermined threshold. Alternatively, it is determined that the scan position of the excitation light beam deviates from the scan target track when the absolute value of the tracking error signal TE2 exceeds a predetermined threshold and the tracking error signal TE2 exceeds the peak. Moreover, in the case where it is determined that the scan position of the excitation light beam deviates from the scan target track based on the amplitude of the tracking error signal TE2 as described above, by making reference to a track number acquired after the determination and then confirming whether this track number is matched with the scan target track number, it may be determined that the scan position of the excitation light beam deviates from the scan target track.

When the controller 215 does not detected that the scan position of the excitation light beam deviates from the scan target track (S31: NO), the controller 215 determines whether the fluorescence detection operation is finished (S38), and monitors the occurrence of track deviation (S31) until the fluorescence detection operation is finished (S38: YES). In this monitoring, when the controller 215 detects that the scan position of the excitation light beam deviates from the scan target track (S31: YES), the controller 215 stops the fluorescence detection operation (S32).

Subsequently, the controller 215 acquires a track number from a track presently scanned at which the excitation light beam is positioned after the occurrence of track deviation, and determines whether the track presently scanned is located on the inner radial side or the outer radial side of the scan target track (S33). When the track presently scanned is located on the outer radial side of the scan target track (S33: NO), the controller 215 jumps the scan position of the excitation light beam to a track one track on the inner radial side of the scan target track (S35), and waits for the arrival of the reference synchronization signal (S36). It is noted that the track jump in S35 is performed by displacing the objective lens 107 similarly to the existing optical disk techniques.

On the other hand, when the track presently scanned is located on the inner radial side of the scan target track (S33: YES), the controller 215 further determines whether the track presently scanned is located on a track one track on the inner radial side of the scan target track (S34). In the case where the track presently scanned is not located on a track one track on the inner radial side of the scan target track (S34: NO), the controller 215 jumps the scan position of the excitation light beam to a track one track on the inner radial side of the scan target track (S35), and waits for the arrival of the reference synchronization signal (S36). Moreover, in the case where the track presently scanned is located on a track one track on the inner radial side of the scan target track (S34: YES), the controller 215 does not make a track jump, and waits for the arrival of the reference synchronization signal (S36).

After the processes, when a signal expressing that the reference synchronization signal is detected is inputted from the reproduction circuit 213 (S36: YES), the controller 215 resumes the fluorescence detection operation (S37). The controller 215 repeatedly performs the processes above until the fluorescence detection operation is finished (S38: YES).

Figure 23B:
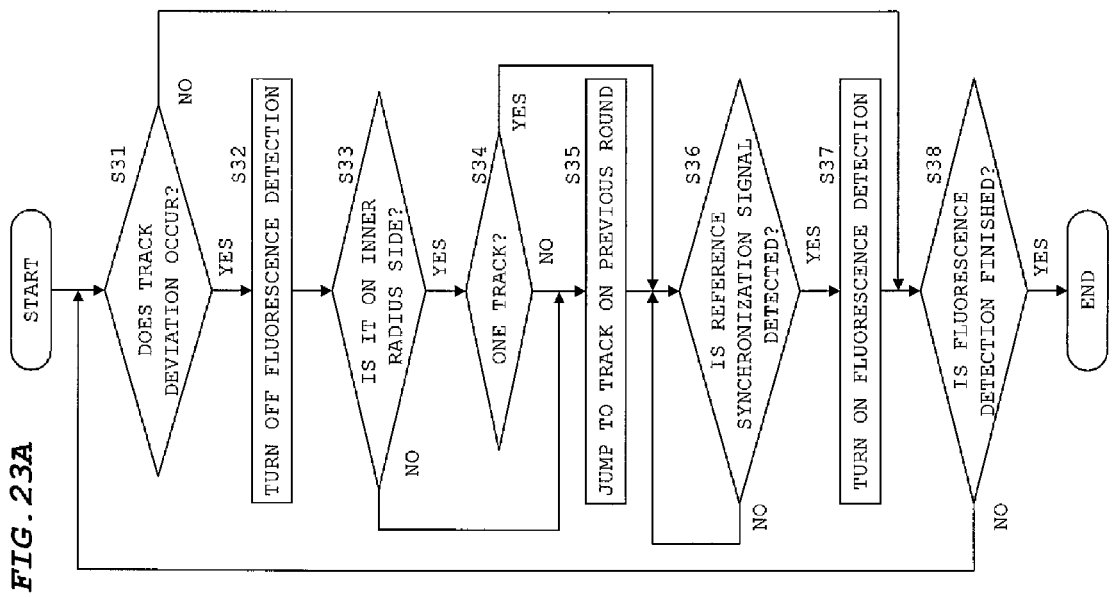

FIG. 23B is a schematic diagram of an exemplary control operation according to the flowchart in FIG. 23A.

Suppose that the excitation light beam is scanned over the track from the position of the reference diameter D0 as depicted by a solid line, and after that, track deviation occurs at position Pa. In this case, suppose that the excitation light beam is positioned at position Pb because of track deviation, as depicted by a thick dotted line in FIG. 23B, the scan position of the excitation light beam is jumped to the track one track on the inner radial side of position Pa. After that, the excitation light beam is scanned over the track after jumped, and the scan position of the excitation light beam reaches the position of the reference diameter D0. Thus, the scan position of the excitation light beam is returned to the beginning position of the track on which track deviation occurs. After that, the fluorescence detection operation is again performed on this track.

Moreover, in the case where the scan position of the excitation light beam is move from position Pa to position Pc because of track deviation, since this position Pc is located on the track one track on the inner radial side of position Pa, the excitation light beam is scanned over this track as it is. When the scan position of the excitation light beam reaches the position of the reference diameter D0, the fluorescence detection operation is again performed on the track on which track deviation occurs.

According to the modification, the following effect can be exerted.

Tracking servo is performed based on the tracking error signal TE1 immediately before the excitation light beam approaches the straight groove while the excitation light beam is scanned over the straight grooves on the well region. On the other hand, tracking servo is performed based on the phase difference of the reflected excitation light beam entered to the photodetector 109, that is, based on the tracking error signal TE1 generated from the general tracking error signal TE, while the excitation light beam is scanned over portions other than the straight grooves on the well region. When the processes are performed by the control circuit 312 in this manner, it is suppressed that tracking servo becomes unstable as compared with the case where tracking servo is performed based on the tracking error signal TE1 all the time.

In other words, when the excitation light beam transmitted through the reflection plane 11a reaches the well layer 12 in the excitation light beam applied to the biosensor substrate 10, a stray light beam caused by the excitation light beam has reached the well layer 12 is entered to the photodetector 109 as described above. In this case, the tracking error signal TE1 is degraded due to the stray light beam, and it is likely that tracking servo becomes unstable.

On the other hand, according to the modification, since tracking servo is performed based on the tracking error signal TE1 immediately before in the period in which the excitation light beam is scanned over the portions of the straight grooves on which the well 13 is disposed, the degradation of tracking servo due to the stray light beam is suppressed. Therefore, such an event can be suppressed that the scan position of the excitation light beam deviates from the track targeted for scanning.

It is noted that in the case where the main cause of track deviation is caused by the eccentricity of the disk, track deviation can be suppressed in advance by setting the length of the region in which servo control performed based on the tracking error signal TE1 is set in the range in which track deviation caused by the eccentricity of the disk does not occur.

Moreover, according to the modification, since the track portions on which the well 13 is disposed are formed of the straight grooves, the diffraction and scattering of fluorescence emitted from the specimen because of the track portions are not easily caused as compared with the case where the track portions are formed of pits or grooves. Thus, a much greater quantity of fluorescence can be stably guided to the fluorescence device 111, so that an excellent fluorescence detection signal can be outputted from the fluorescence device 111.

Furthermore, the tracking error signal TE2 is generated based on the phase difference of the reflected excitation light beam entered to the photodetector 109 even when the excitation light beam is scanned over the straight grooves. Thus, the controller 215 can determine whether the scan position deviates from a target track based on the tracking error signal TE2, and can correctly perform the fluorescence detection operation on the track on which track deviation occurs in accordance with the flowchart illustrated in FIG. 23A.

In addition, the period of the well synchronization signal (one TM and one TS) is set shorter than the period of the reference synchronization signal (two TMs and two TSs); a large number of the well synchronization signals exist in the zone, and only one reference synchronization signal exists in the zone. Thus, the region occupied by the well synchronization signals can be made smaller, and a large number of the well regions can be disposed in the zone. As a result, the zones can be effectively used.

As described above, the embodiment of the present invention is described. The present invention is not limited to the foregoing embodiment at all, and the embodiment of the present invention can be variously modified other than the foregoing embodiment.

For example, in the foregoing embodiment, red blood cells are accommodated in the well 13, and it is determined whether red blood cells are infected with malaria parasites. However, a specimen to be accommodated in the well 13 and an event targeted for determination are not limited to them.

For example, it may be fine that a cell expressing a certain gene or a cell including a greater amount or a shorter amount of a living substance such as a nucleic acid, protein, lipid, and sugar than in a normal amount is detected as a certain cell from various cell groups. This certain cell may be cells exit in the natural world, or cells artificially processed. Although cells exiting in the natural world are not limited more specifically, the cells include, for example, a pathogenic cell, lesion cell, cell infected with a pathogenic bacteria or pathogenic organism, mutant cell, unknown cell including a specific nature, and the like. Moreover, although artificial processes are not limited more specifically, the processes include, for example, a physical process (for instance, electromagnetic wave application), chemical process (for instance, drug treatment), genetic engineering process (for instance, genetic modification processing), and the like.

Furthermore, it may be fine that in these artificial processes, a process whose influence on cells is known is applied to a cell group and a cell that does not exhibit the influence or a cell that strongly exhibits the influence is detected as a certain cell. For example, a cell resistant to or highly sensitive to drug treatment can be detected as a certain cell.

In addition, the types of cell groups are not limited more specifically as well. The cell groups may be groups of cells derived from multicellular organisms in addition to groups of unicellular organisms. Cells derived from a multicellular organism include, for example, a cell obtained from normal tissue or pathological tissue of an organism, a cultured cell derived from these cells, and the like. Moreover, organisms from which these cells are obtained are not limited more specifically. For example, cells may be cells derived from animals, or cells derived from plants. More specifically, detection target cells include, for example, cells derived from vertebrate animals (more specifically mammals and birds), cells derived from insects, plant cultured cells, and the like. However, a detection target cell is not limited to these cells. Furthermore, cell groups may be groups of the same cells or may be groups including a plurality of types of cells.

In addition, in the foregoing embodiment, the region in which the well 13 is disposed is divided according to the zone number held on the reference region. However, the region on which information to divide the region on which the wells 13 are disposed into a plurality of zones is held is not limited to the reference region, and the region may be other regions. For example, it may be fine that information to divide the region on which the wells 13 are disposed into a plurality of zones is held on the management zone illustrated in FIG. 2A. In this case, the track numbers continuing in the radial direction from the innermost radius of the biosensor substrate 10 toward the outer radial direction are held on the reference region, and information that defines the start position and the end position of the zones is held on the management zone.

For example, in the case where the width of the zones in the radial direction is a width of 300 tracks, information to set the range of the zone according to a track number is held on the management zone as a range of track numbers 1 to 300 is zone 1 and the range of track numbers 301 to 600 is zone 2. The velocities of the biosensor substrate 10 are updated in accordance with an event that a track number acquired from the present scan position of the excitation light beam is shifted from a range of track numbers defining one zone to a range of track numbers defining another zone.

Moreover, in the foregoing embodiment, the angular velocity is set to the zones in such a manner that the linear velocity to the track on the innermost radius of the individual zones is constant. However, it may be fine that the angular velocity is set to the zones in such a manner that the linear velocity to the track on the outermost radius on the zones is constant, or it may be fine that the angular velocity is set to the zones in such a manner that the linear velocity to the tracks at the same positions in the radial direction is constant in the zones.

Furthermore, it may be fine that the linear velocity to the track on the innermost radius of the individual zones is not necessarily the same between the zones, or it may be fine that the linear velocity to the track on the innermost radius of the individual zones is slightly displaced with each other. It may be fine that the angular velocity is set to the zones in such a manner that the linear velocity to the track on the innermost radius of the individual zones is varied as long as a sufficient light beam quantity of an excitation light beam is applied to the specimen in the well 13 included in the zones and scanning over the biosensor substrate 10 is finished more quickly than the case where the region on which the wells 13 are disposed is scanned at a constant linear velocity.

In addition, in the foregoing embodiment, the wells 13 are disposed on the zones in such a manner that the wells 13 are arranged in one round on one zone. However, it may be fine that the wells 13 are disposed on the zones in such a manner that the wells 13 are arranged in two rounds or greater on one zone.

Figure 24A:
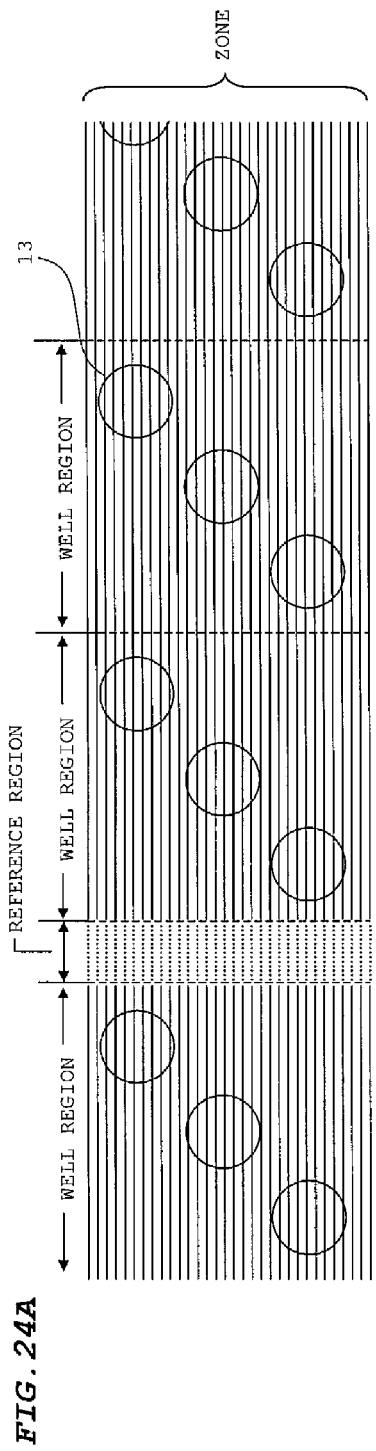
FIGS. 24A to 24C are diagrams of the arrangement forms of wells to zones according to another modification.
Figure 24B:
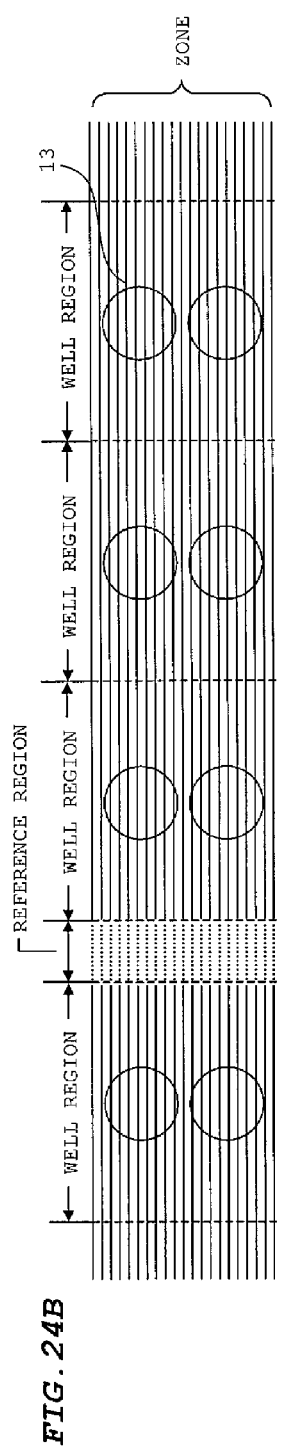
Figure 24C:
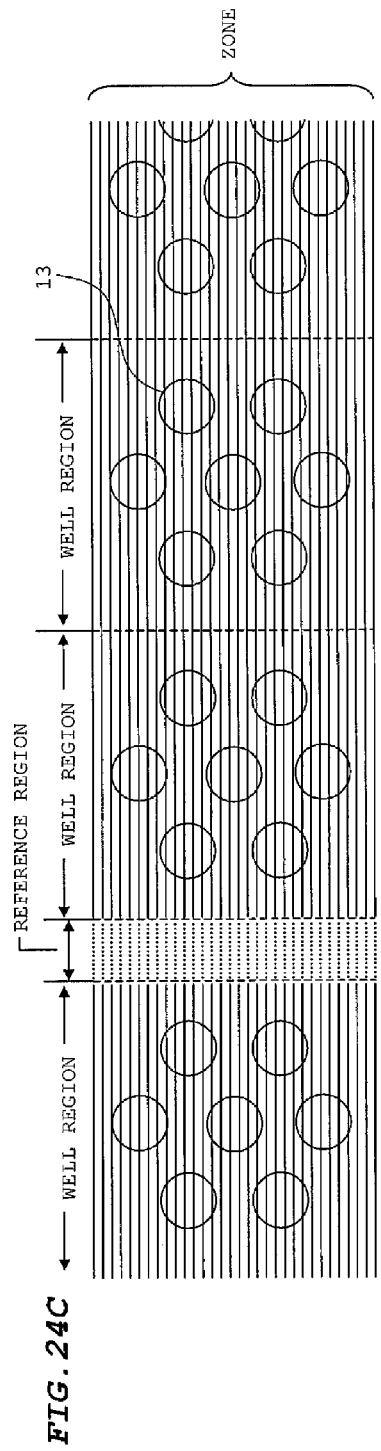

For example, it may be fine that as illustrated in FIG. 24A, the wells 13 are disposed in such a manner that the wells 13 in three rounds are disposed on one zone and the wells 13 are displaced in the radial direction and the circumferential direction on the zones. Alternatively, it may be fine that as illustrated in FIG. 24B, the wells 13 are disposed in such a manner that the wells 13 in two rounds are disposed on one zone and two wells 13 are arranged in the radial direction and not displaced in the circumferential direction on one zone. Moreover, it may be fine that as illustrated in FIG. 24C, the wells 13 are disposed in such a manner that a group formed of a plurality of the wells 13 is arranged at constant spacings in the circumferential direction on one zone.

Furthermore, in the foregoing embodiment, the same number of the well 13 is disposed on all the zones. However, it may be fine that the number of the wells 13 disposed on the zones is varied between the zones. For example, as long as the distance in the circumferential direction between the wells 13 adjacent in the circumferential direction is the same, the number of the wells 13 disposed on one zone is greater on the zone on the outer radial side than on the zone on the inner radial side. It may be fine that the number of the wells 13 disposed on the zones is set as described above in such a manner that the number of the wells 13 disposed on the zone is more increased as the position of the zone goes toward on the outer radial side of the biosensor substrate 10. In this case, the wells 13 are not arranged in the radial direction of the biosensor substrate 10.

In addition, in the foregoing embodiment, the reflective film 14 is formed of a metal. However, the reflective film 14 is not limited to a metal, and may be formed of a translucent dielectric material. In this case, the refractive index of the base substrate 11 is different from the refractive index of the dielectric material, and reflection can be made. More specifically, polycarbonate (a refractive index of 1.59) can be used for the material of the base substrate 11, and $TiO_2$ (a refractive index of 2.65) can be used for the material of the reflective film 14, for example. Moreover, niobium oxide ($Nb_2O_5$) is used for the material of the reflective film 14, a reflectance near a wavelength of 400 nm can be increased, and a reflectance near a wavelength of 500 nm can be decreased, so that such a reflective film 14 can be provided that a reflectance R1 for the excitation light beam is increased and a reflectance R2 for fluorescence is decreased. Furthermore, a stacked film of a dielectric film and a metal film may be used for the reflective film 14.

In addition, in the foregoing embodiment, as illustrated in FIG. 1A, the shape of the well 13 is set in a cylindrical shape, but not limited to this shape. However, it may be fine that the shape of the well 13 is set in a shape other than a cylindrical shape such as a quadrangular prism, elliptic cylinder, cone, and pyramid as long as a specimen can be accommodated. Moreover, the diameter d1 and the height d2 of the well 13, the spacing d3 between the bottom portion 13a and the reflection plane 11a, the spacing d4 of the well 13, the thickness d5 of the base substrate 11, and the track pitch d6 of the reflection plane 11a are not limited to the values in the foregoing embodiment, and the values may be appropriately set.

Furthermore, in the foregoing embodiment, the wavelength of the excitation light beam emitted from the semiconductor laser 101 is set to 405 nm. However, the wavelength is not limited to this, and may be appropriately set according to types of fluorescence labeling used for a specimen targeted for measurement. Various parameters of the optical system such as the transmission wavelength range of the dichroic prism 106 are appropriately changed in accordance with changes in the wavelengths of the excitation light beam and fluorescence.

In addition, in the foregoing embodiment, as illustrated in FIGS. 5A to 5D, the biosensor substrate 10 is fabricated in which the base substrate 11 is shaped by injection molding, the reflective film 14 is deposited on the top face of the reflection plane 11a, the bottom layer 12a is stacked by spin coating, and the top layer 12b is formed by photo-polymerization molding. However, the fabrication method for the biosensor substrate 10 is not limited to this method, and the biosensor substrate 10 may be fabricated by different methods appropriately.

Moreover, in the foregoing embodiment, information is held on the pit strings. However, it may be fine that information is held in which the track is formed in a groove with no pits and this groove is caused to meander in the radial direction of the biosensor substrate 10. In this case, information is held by the meandering waveform of the groove. Furthermore, the meandering shape of the groove can be reproduced based on the tracking error signal similarly to techniques applied to existing optical disks. In addition, it may be fine that information is held by a combination of a pit and a groove.

Moreover, in the foregoing embodiment, it may be fine that a lid is provided above the well 13 in rotating the biosensor substrate 10 by the rotating device 123. Thus, it is possible to prevent undesirable drain (an unintended drain), evaporation, or movement of a specimen out of the well 13.

Figure 25:
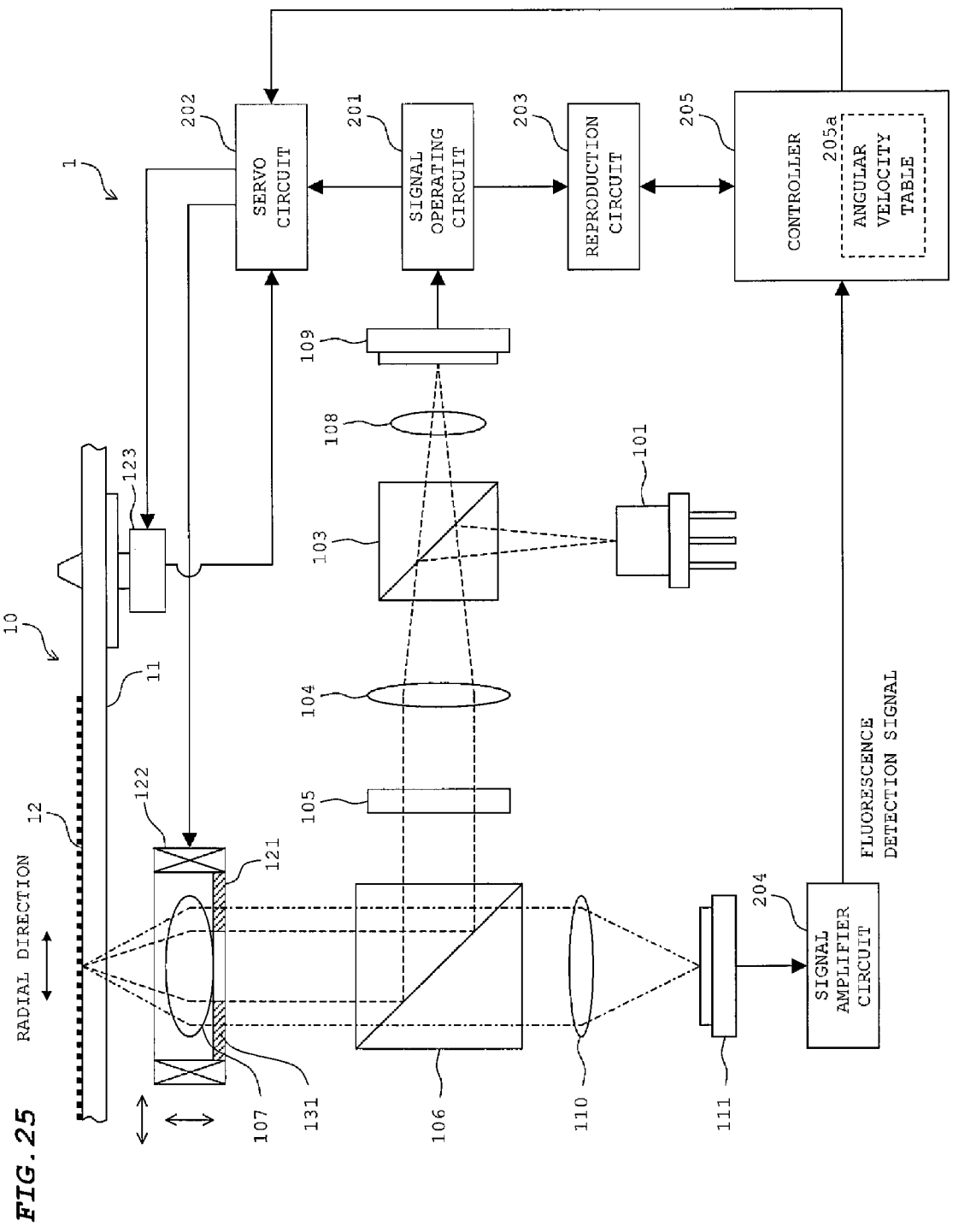
FIG. 25 is a diagram of the optical system of a fluorescence detector according to still another modification.

Furthermore, the optical system of the fluorescence detector 1 is not limited to one illustrated in FIG. 7, which can be variously modified in addition to this. For example, it may be fine that as illustrated in FIG. 25, the aperture 102 is omitted from the optical system illustrated in FIG. 7 and a circular aperture 131 is disposed on the dichroic prism 106 side of the holder 121 instead of the aperture 102. In this configuration, the aperture 131 has a wavelength selectivity, and is configured in which a predetermined peripheral portion is shielded to the excitation light beam and fluorescence is transmitted through all the portions. Similarly, it may be fine that the aperture 102 is omitted from the optical system in FIG. 18 and a circular aperture is disposed on the dichroic prism 106 side of the holder 121 instead of the aperture 102.

In addition, in the foregoing embodiment, one semiconductor laser 101 is used as a light source. However, the present invention is also applicable to a fluorescence detector including an optical system other than ones described above and a specimen holding carrier in a configuration other than ones described above. For example, the present invention is also applicable to a fluorescence detector including a light source that applies an excitation light beam to a well and a light source that applies the laser light beam to a track separately and to a specimen holding carrier used for the same.

Moreover, in modification 5 described above, the track portions on the well region corresponding to the well synchronization signal, the track number, and the well number are formed of pit strings. However, it may be fine that the track is formed of continuous grooves, or it may be fine that track is formed of a combination of a pit string and a groove. In the case where the track is formed of grooves, grooves are caused to meander, for example, and various items of information are held. In other words, the meandering shape of the groove is modulated based on information to be held on the track. It may be fine that all the pit strings on the biosensor substrate 10 according to modification 5 described above are replaced by a groove (groove) and various signals and various items of information are held by the meandering of the groove. In this case, various synchronization signals are distinguished from other signals based on the unique pattern of the meandering shape of the groove.

Figure 26:
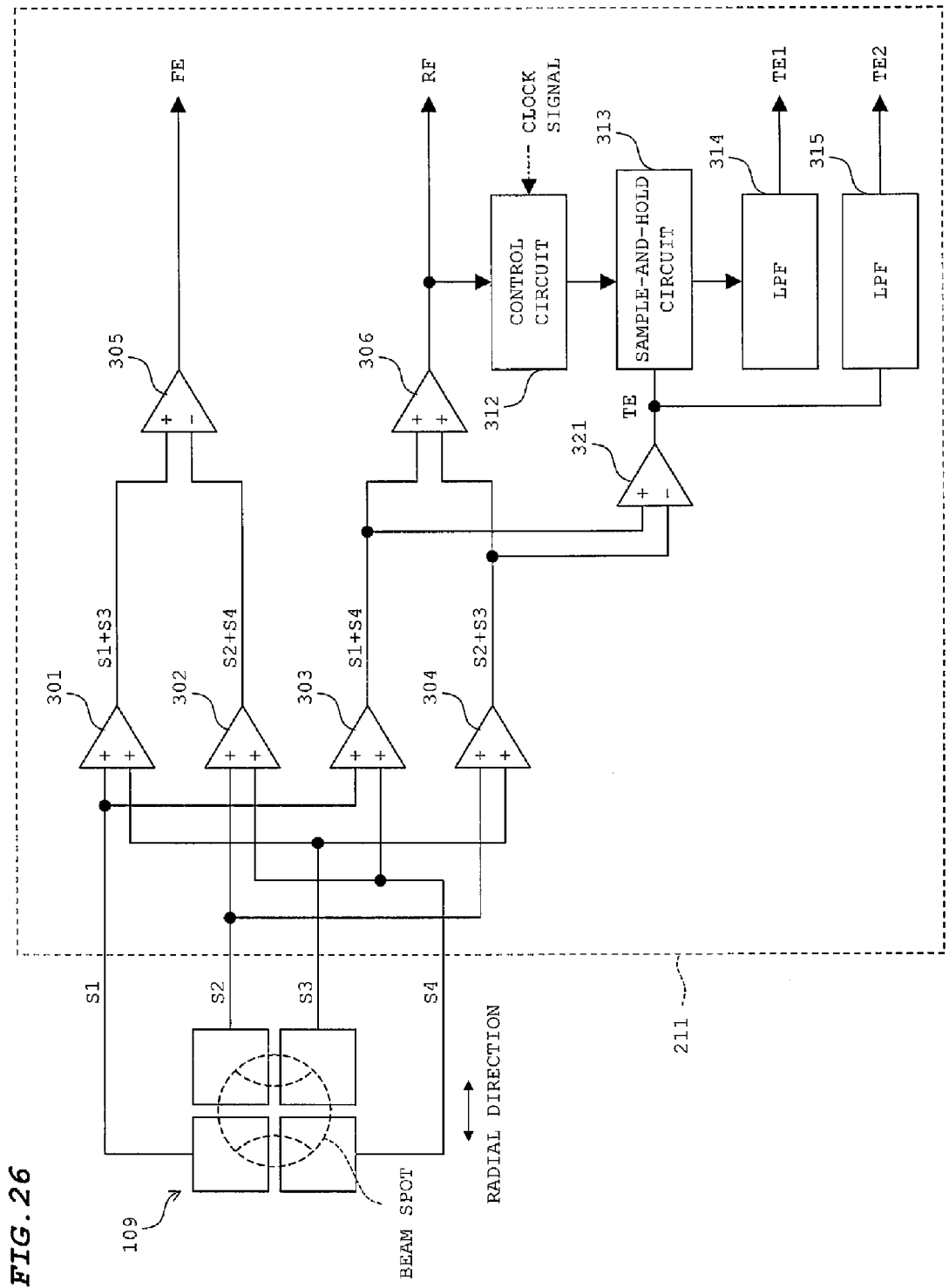
FIG. 26 is a diagram of the configuration of a signal operating circuit in the case where all of pit strings on a biosensor substrate are replaced with grooves (grooves) according to yet another modification.

FIG. 26 is a diagram of the configuration of a signal operating circuit 211 in the case where all the pit strings on the biosensor substrate 10 according to modification 5 described above are replaced by the grooves (groove) as described above.

In the signal operating circuit 211, a generation method for the tracking error signal is changed to a DPP (differential Push-Pull) method from the DPD method. Accordingly, the phase difference detection circuit 311 in FIG. 19 is replaced by a subtractor 321, and a signal line connected to the input terminal of the subtractor 321 is changed from the signal operating circuit 211 in FIG. 19.

The subtractor 321 generates the tracking error signal TE by subtracting the added value (S1+S4) of the outputs of two sensors on the left side split by a split line perpendicular to the radial direction and the added value (S2+S3) of the outputs of two sensors on the right side split by the split line in four sensors configuring the quadrant sensor of the photodetector 109. The circuit configuration on the subsequent stage side of the subtractor 321 is similar to the case in FIG. 19. Moreover, the functions of the control circuit 312 and the sample-and-hold circuit 313 are also similar to the case in FIG. 19.

Also in an exemplary configuration in FIG. 26, similarly to modification 5 described above, in the period in which the excitation light beam is scanned over the meandering groove, the sample-and-hold circuit 313 is opened, and tracking servo is performed using the general tracking error signal TE1. Furthermore, in the period in which the excitation light beam is scanned over the straight grooves, the tracking error signal TE1 immediately before is held (retained), and tracking servo is performed using the held (retained) tracking error signal TE1. Therefore, the effect similar to the effect in modification 5 described above can be exerted by this exemplary configuration as well.

In addition, in the exemplary configuration in FIG. 26, the meandering shape of the groove is acquired from the tracking error signal TE1 outputted in the period in which the excitation light beam is scanned over the meandering groove, and various synchronization signals and various items of information such as a zone number are acquired according to the acquired meandering shape. In other words, the reproduction circuit 213 acquires the meandering shape of the groove based on the tracking error signal TE1, and acquires various synchronization signals and various items of information such as a zone number based on the acquired meandering shape. It is noted that a method for acquiring the synchronization signals and various items of information from the meandering groove can be implemented using the existing optical disk techniques.

Moreover, in modification 5 described above, the track portions on which the well 13 on the well region is disposed are formed of straight grooves. However, it may be fine that the straight grooves are omitted and a region near the region on which the well 13 on the well region is disposed is formed in a mirror-finished surface.

Figure 27:
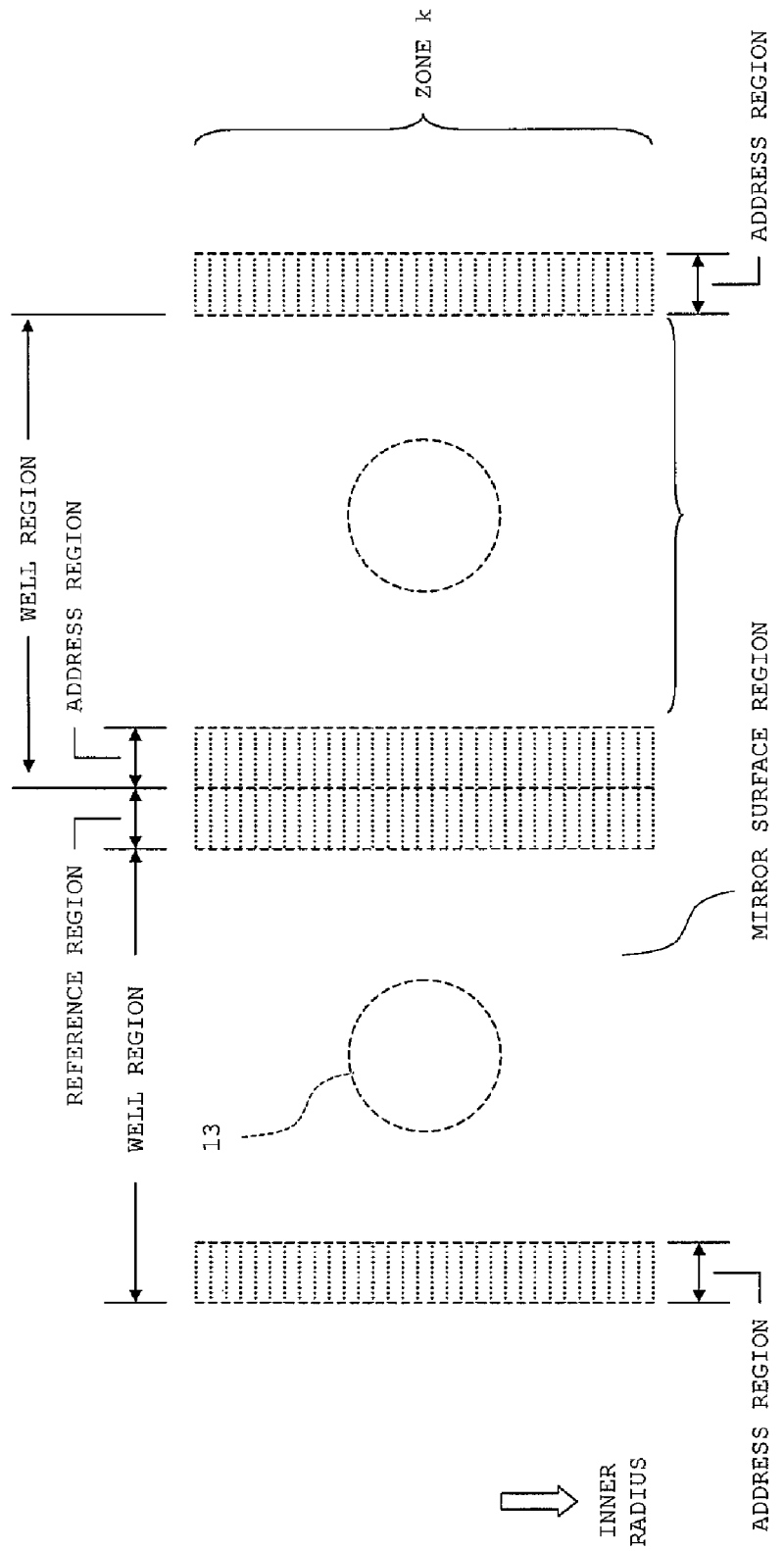
FIG. 27 is a diagram of the area allocation of a biosensor substrate in the case where regions near regions where wells are arranged are formed in a mirror-finished surface according to still yet another modification.

FIG. 27 is a diagram of the area allocation of the biosensor substrate 10 in this case. In this configuration, the pit strings to hold the information are formed on the address region of the well region on the top face of the base substrate 11, and the region subsequent to the pit strings is formed in a flat surface with no straight grooves. The reflective film 14 is formed on the flat surface as well, and the surface of the reflective film 14 is a flat mirror surface.

According to this configuration, fluorescence emitted from the specimen accommodated in the well 13 is not scattered and diffracted by the straight grooves, so that fluorescence in a greater light beam quantity can be further stably guided to the fluorescence device 111 as compared with the foregoing embodiment.

It is noted that in modification 5 described above, since general tracking servo based on the degree of application of the excitation light beam to the straight grooves is not performed in the period in which the excitation light beam is scanned over the straight grooves in the well region, a problem does not occur specifically in tracking servo even though straight grooves are omitted as in the exemplary configuration in FIG. 27. However, in this configuration, since the tracking error signal TE2 based on the straight grooves is not enabled to be generated, it is not possible to detect that the scan position of the excitation light beam deviates from the target track based on the tracking error signal TE2 as in the foregoing embodiment. Therefore, in the case of this exemplary configuration, a track number is acquired from the address region of the subsequent well region coming after the mirror surface region is passed through and it is detected that the scan position of the excitation light beam deviates from the target track based on an event that the acquired track number is different from the track number acquired from the previous well region, for example.

It is noted that in the case of the exemplary configuration in FIG. 27, since the tracking error signal TE2 based on the straight grooves is not enabled to be generated as described above, the LPF 315 is omitted from the configuration of FIG. 19 or FIG. 26.

Moreover, in modification 5 described above, the sample-and-hold circuit 313 is controlled by the control circuit 312. However, the sample-and-hold circuit 313 may be controlled by the controller 215.

Furthermore, in modification 5 described above, the sample-and-hold circuit 313 is disposed in the signal operating circuit 211. However, it may be fine that the sample-and-hold circuit 313 is disposed to hold (retain) a tracking servo signal (a drive signal applied to the objective lens actuator 122) outputted from the servo circuit 212.

Figure 28:
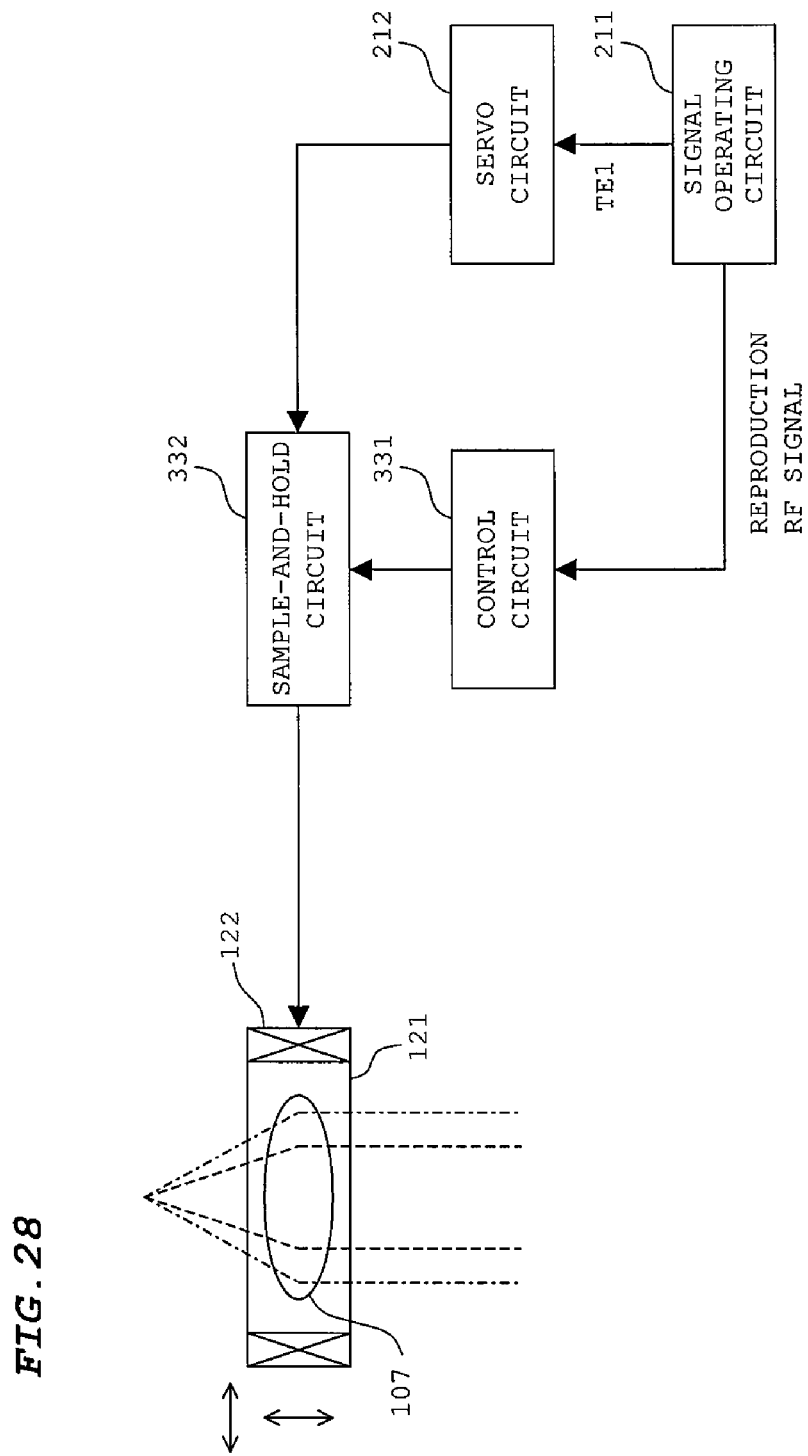
FIG. 28 is a diagram of the configuration in the case where a tracking servo signal outputted from a servo circuit is held according to still another modification.

FIG. 28 is a diagram of the configuration of this case. Similarly to modification 5 described above, in the period in which the tracking servo signal immediately before the excitation light beam approaches the straight groove is held (retained) by the sample-and-hold circuit 332 and the excitation light beam is scanned over the straight grooves, the control circuit 331 uses the held (retained) tracking servo signal to control the objective lens actuator 122 in the tracking direction. In this case, since the tracking servo signals having the same value are continuously supplied to the objective lens actuator 122, the excitation light beam is fixed at the position immediately before the excitation light beam approaches the straight groove. After that, when the excitation light beam goes through the straight groove, the control circuit 331 opens the sample-and-hold circuit 332, and performs general tracking servo based on the tracking error signal TE1.

Moreover, control to stabilize tracking servo illustrated in FIG. 21 and control when the scan position of the excitation light beam deviates from a scan target track illustrated in FIG. 23A in modification 5 described above can be also applied to the case of using a biosensor substrate 10 for the measurement of the fluorescence detector 1, in which the region on which the wells 13 are formed are not sectioned into a plurality of zones. In this case, the servo circuit 212 can control the rotating device 123 in such a manner that the biosensor substrate 10 is rotated at a constant linear velocity using the clock signal outputted from the clock generator circuit 216. Thus, the tracks on the biosensor substrate 10 are scanned with the excitation light beam at a constant linear velocity.

In addition to this, the embodiment of the present invention can be appropriately and variously modified within the scope of the technical ideas described in claims.

The invention claimed is:

1. A fluorescence detector that applies a light beam to a specimen holding carrier holding a fluorescently-labeled specimen and detects fluorescence emitted from the specimen by applying the light beam, wherein:
the specimen holding carrier includes:
a substrate;
a track formed to turn around a center of the substrate; and
a plurality of specimen accommodating portions disposed on a top face side of the substrate and accommodating a specimen, wherein:
a region on which the specimen accommodating portions are disposed is sectioned into a plurality of zones in a radial direction; and
the specimen accommodating portions are arranged in a circumferential direction of the substrate in the zones;
the fluorescence detector includes:
a rotation drive unit configured to rotate the specimen holding carrier;
a projection unit configured to cause the light beam to follow the track;
a detection unit configured to detect fluorescence emitted from the specimen; and
a rotation control unit configured to control the rotation drive unit; and
the rotation control unit rotates the specimen holding carrier at a same angular velocity in a period in which the light beam is applied to one zone, and changes the angular velocity to the zone so that the angular velocity to the zone becomes smaller as the position at which the zone is disposed goes toward an outer radial side of the substrate.

2. The fluorescence detector according to claim 1, wherein the rotation control unit sets an angular velocity to the zones so that a velocity when the light beam is scanned over a track located at a position apart at a predetermined distance from a boundary of the zone in the radial direction of the substrate is almost the same in all of the zones.

3. The fluorescence detector according to claim 1, wherein the projection unit includes: a light source configured to emit the light beam;
an objective lens configured to converge the light beam on the specimen holding carrier;
a lens drive unit configured to drive the objective lens at least in a direction crossing the track;
a photodetector configured to receive the light beam reflected on the specimen holding carrier;
a signal operating unit configured to generate a tracking error signal expressing positional displacement of a scan position of the light beam to the track in the direction crossing the track based on an output signal of the photodetector;
a tracking control unit configured to control the lens drive unit based on the tracking error signal generated at the signal operating unit; and
a control switching unit configured to stop control of the lens drive unit based on the tracking error signal and keep a control state of the lens drive unit to a control state before stopped in a period in which the light beam is scanned over a region corresponding to the specimen accommodating portion.

4. The fluorescence detector according to claim 3, wherein the control switching unit includes a signal holding unit configured to hold the tracking error signal immediately before control of the lens drive unit is stopped and output the held tracking error signal to the tracking control unit.

5. The fluorescence detector according to claim 4, wherein:
the track is formed with a unique structure at a position displaced in a direction opposite to a scanning direction of the light beam with respect to a region corresponding to the specimen accommodating portion; and
the signal holding unit holds the tracking error signal when the unique structure is detected based on a detection signal from the photodetector.

6. The fluorescence detector according to claim 3, wherein the control switching unit includes a signal holding unit configured to hold a signal to the lens drive unit immediately before control of the lens drive unit is stopped and output the held signal to the lens drive unit.

7. The fluorescence detector according to claim 6, wherein:
the track is formed with a unique structure at a position displaced in a direction opposite to a scanning direction of the light beam with respect to a region corresponding to the specimen accommodating portion; and
the signal holding unit holds the tracking error signal when the unique structure is detected based on a detection signal from the photodetector.

8. The fluorescence detector according to claim 3, further comprising a track deviation detection unit configured to detect that a scan position of the light beam deviates from a track targeted for scanning in a period in which the light beam is scanned over a region corresponding to the specimen accommodating portion,
wherein the tracking control unit controls the lens drive unit to return the scan position of the light beam to the track targeted for scanning based on a detection by the track deviation detection unit that the scan position of the light beam deviates from the track targeted for scanning.

9. The fluorescence detector according to claim 8, wherein:
the track is formed on a region corresponding to the specimen accommodating portion of the specimen holding carrier so that the track continuously extends in a scanning direction of the light beam; and
the track deviation detection unit monitors the tracking error signal in a period in which the light beam is scanned over a region corresponding to the specimen accommodating portion, and detects that a scan position of the light beam deviates from the track targeted for scanning based on a state of the tracking error signal.

10. The fluorescence detector according to claim 8, wherein:
on the specimen holding carrier, the track is not formed on a region corresponding to the specimen accommodating portion, and an address on a track is held on the track at a position displaced in a direction opposite to a scanning direction of the light beam with respect to the region corresponding to the specimen accommodating portion; and the track deviation detection unit detects that a scan position of the light beam deviates from the track targeted for scanning based on the address acquired from the track after the scan position of the light beam is passed through the region corresponding to the specimen accommodating portion.

* * * * *